US008436180B2

(12) United States Patent
Bärfacker et al.

(10) Patent No.: US 8,436,180 B2
(45) Date of Patent: May 7, 2013

(54) SUBSTITUTED-4-ARYL-1,4-DIHYDRO-1,6-NAPHTHYRIDINAMIDES AND USE THEREOF

(75) Inventors: Lars Bärfacker, Oberhausen (DE); Peter Kolkhof, Wuppertal (DE); Karl-Heinz Schlemmer, Wuppertal (DE); Rolf Grosser, Leverkusen (DE); Adam Nitsche, Pulheim (DE); Martina Klein, Heiligenhaus (DE); Klaus Münter, Wülfrath (DE); Barbara Albrecht-Küpper, Wülfrath (DE); Elke Hartmann, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 418 days.

(21) Appl. No.: 12/526,951

(22) PCT Filed: Feb. 19, 2008

(86) PCT No.: PCT/EP2008/001257
§ 371 (c)(1),
(2), (4) Date: Jan. 12, 2010

(87) PCT Pub. No.: WO2008/104306
PCT Pub. Date: Sep. 4, 2008

(65) Prior Publication Data
US 2010/0136142 A1 Jun. 3, 2010

(30) Foreign Application Priority Data
Feb. 27, 2007 (DE) .................... 10 2007 009 494

(51) Int. Cl.
*C07D 471/02* (2006.01)
*A61K 31/44* (2006.01)

(52) U.S. Cl.
USPC .......................................... 546/122; 514/300

(58) Field of Classification Search .................. 546/122; 514/300
See application file for complete search history.

(56) References Cited

U.S. PATENT DOCUMENTS

| 4,698,341 | A | 10/1987 | Satzinger et al. |
| 4,711,901 | A | 12/1987 | Satzinger et al. |
| 4,751,228 | A | 6/1988 | Kleinschroth et al. |
| 4,760,081 | A | 7/1988 | Satzinger et al. |

FOREIGN PATENT DOCUMENTS

| CA | 2615855 A1 | 1/2007 |
| EP | 0133530 A2 | 2/1985 |
| EP | 0173933 A1 | 3/1986 |
| EP | 0189898 A1 | 8/1986 |
| EP | 0234516 | 4/1992 |
| WO | WO 2005/087740 | 9/2005 |
| WO | WO-2005/097118 A1 | 10/2005 |
| WO | WO-2006/066011 A2 | 6/2006 |
| WO | WO 2007/009670 | 1/2007 |
| WO | 02/10164 A2 | 2/2007 |
| WO | WO 2007/040934 | 4/2007 |
| WO | WO 2007/140894 | 12/2007 |

OTHER PUBLICATIONS

Kelly, et. al., "Cortisol and hypertension", Hcaplus Abstract 1998:717826 (1998).*
West, Anthony R., Solid State Chemistry and its Applications, Wiley, New York, 1988, pp. 358 & 365.*
Zannad et al., "Effect of MR Blockade on Callagen Formation and Cardiovascular Disease with a Specific Emphasis on Heart Failure", Heart Failure REviews, 10, 71-78, 2005.*
Rocha et. al., "Rationale for the Use of Aldosterone Antagonists in Congestive Heart Failure", Drugs, 2002, 62(5): 723-731.*
R. E. Booth et al.: "Aldosterone," Advances in Physiology Education, vol. 26, No. 1, Mar. 2002, pp. 8-20.
B. Pitt et al.: "Eplerenone, A Selective Aldosterone Blocker, in Patients with Left Ventricular Dysfunction after Myocardial Infarction," The New England Journal of Medicine, vol. 348, No. 14, Apr. 3, 2003, pp. 1309-1321.
B. Pitt et al.: "The Effect of Spironolactone on Morbidity and Mortality in Patients with Severe Heart Failure," The New England Journal of Medicine, vol. 341, No. 10, pp. 709-717.
L. Seiler et al.: "Der Aldosteron-Renin-Quotient bei Sekundarer Hypertonie," Herz, vol. 28, No. 8, 2003, 686-691.
H. A. Kuhn et al.: Innere Medizin—Ein Lehrbuch fur Studierende der Medizin and Arzte Begrundet von Ludwig Heilmeye, Springer-Verlag, Berlin, Heidelberg, New York, 1982.
M. A. Zaman et al.; "Drugs Targeting the Renin-Angiotension-Aldosterone System," Nature Reviews Drug Discovery, vol. 1, Aug. 2002, pp. 621-636.
G. Werner et al.: "Hydrophobic Properties of Novel Dihydronaphthyridine Calcium Antagonists and Biological Activity in Porcine Isolated Cardiac and Vascular Smooth Muscle," Naunyn-Schmiedeberg's Archives of Pharmacology vol. 344, 1991, pp. 337-344.
Barabanov, et al.:" Functionalized Naphtho [2,3-h] quinoline-7,12-diones," Russian Chemical Bulletin, Nov. 1998, 47(11):2256-2261.
Funder, "Mineralcorticoid Receptors and Cardiovascular Damage: It's Not Just Aldosterone," Hypertension, 2006, 47:634-635.
Hayashi, et al.:"Immediate Administration of Mineralocorticoid Receptor Antagonist Spironolactone Prevents Post-Infarct Left Ventricular Remodeling Associated With Suppression of a Marker of Myocardial Collagen Synthesis in Patients With First Anterior Acute Myocardial Infarction," Circulation, May 2003, 107(20):2559-2565.
Kleinschroth, et al.:" Synthese Neur 1,6-Naphthyridine durch Aminomethin-ylierung von 1,4-Dihydropyridinen," Synthesis, Oct. 1986, pp. 859-860.
McNamara, et al.:"Synthesis and antitumor activity of fluorine-substituted 4-amino-2(1H)-pyridinones and their nucleosides. 3-Deazacytosines," J. Med. Chem., 1987, 30:340-347.

(Continued)

*Primary Examiner* — John Mabry
(74) *Attorney, Agent, or Firm* — Karen B. King

(57) ABSTRACT

The present application relates to novel substituted 4-aryl-1,4-dihydro-1,6-naphthyridine-3-carboxamides, a process for their preparation, their use for the treatment and/or prophylaxis of diseases, and their use for the manufacture of medicaments for the treatment and/or prophylaxis of diseases, especially cardiovascular disorders.

10 Claims, No Drawings

OTHER PUBLICATIONS

Moseley: "Alternative Esters in the Synthesis of ZD0947," Tetrahedron Letters, May 2005, 46(18):3179-3181.

Nesnow, et al.:"Pyridine Nucleosides Related to 5-Fluorocytosine," J. Heterocycl. Chem., 1975, 12:941-944.

Pietzonka, et al.:"Alkylations of (R,R)-2-t-Butyl-6-methyl-1,3-dioxan-4-ones which are not Possible with Lithium Amides may be Achieved with a Schwesinger P4 Base," Chemische Berichte, Jan. 25, 2006, 124(8):1837-1843.

Pitt, et al.:"The Effect of Spironalactone on Morbidity and Mortality in Patients with Severe Heart Failure," The New England Journal of Medicine, Sep. 2, 1999, 341(10):709-717.

Pitt, et al.:""Neurohumoral Effects of Aliskiren in Patients with Symptomatic Heart Failure Receiving a Mineralocorticoid Receptor Antagonist: The Aliskiren Observation of Heart FailureTreatment study,"" European Journal of Heart Failure, 2011, 13(7): 755-764.

Schmidt, et al.:"Cardioprotective Effects of Mineralocorticoid Receptor Antagonists at Reperfusion," European Heart Journam, 2010, 31:1655-1662.

Schwesinger, et al.:"Peralkylated Polyaminophosphazenes-Extremely Strong, Neutral Nitrogen Bases," Angewandte Chemie International Edition in English, Dec. 22, 2003, 26(11):1167-1169.

Searls, et al.:"Synthesis of the Analogue Nucleoside 3-Deaza-2'-Deoxycytidine and its Template Activity with DNA Polymerase," Tetrahedron, 1999, 55:11985-11996.

Takeda:"Pleiotropic Actions of Aldosterone and the Effects of Eplerenone, a Selective Mineralocorticoid Receptor Antagonist," Hypertens. Res., 2004, 27(11):781-789.

Weihong, "Sterioid Receptor Heterodimerization Demonstrated in vitro and in vivo," Proc Natl. Acad. Sci USA, Dec. 1995, 92:12480-12484.

U.S. Appl. No. 12/303,719, 371 date Jun. 28, 2010.

U.S. Appl. No. 12/303,369, filed Aug. 7, 2009.

* cited by examiner

SUBSTITUTED-4-ARYL-1,4-DIHYDRO-1,6-NAPHTHYRIDINAMIDES AND USE THEREOF

RELATED APPLICATIONS/PATENTS AND INCORPORATION BY REFERENCE

This application is a National Stage Application filed under 35 U.S.C. §371 based on International Application No. PCT/EP2008/001257, filed Feb. 19, 2008, which claims priority to German Patent Application Number 102007009494.0, filed Feb. 27, 2007, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel substituted 4-aryl-1,4-dihydro-1,6-naphthyridine-3-carboxamides, a process for their preparation, their use for the treatment and/or prophylaxis of diseases, and their use for the manufacture of medicaments for the treatment and/or prophylaxis of diseases, especially cardiovascular disorders.

Aldosterone plays a key part in maintaining fluid and electrolyte homeostasis by promoting, in the epithelium of the distal nephron, sodium retention and potassium secretion, thus contributing to keeping the extracellular volume constant and thus to regulating blood pressure. Besides this, aldosterone displays direct effects on the structure and function of the cardiac and vascular system, but the underlying mechanisms thereof are not yet fully explained [R. E. Booth, J. P. Johnson, J. D. Stockand, *Adv. Physiol. Educ.* 26 (1), 8-20 (2002)].

Aldosterone is a steroid hormone which is formed in the adrenal cortex. Its production is regulated indirectly very substantially depending on the renal blood flow. Any decrease in renal blood flow leads to release in the kidney of the enzyme renin into the circulating blood. This in turn activates the formation of angiotensin II, which on the one hand has a constricting effect on the arterial blood vessels, but on the other hand also stimulates the formation of aldosterone in the adrenal cortex. Thus, the kidney acts as blood pressure sensor, and thus indirect volume sensor, in the circulating blood and counteracts, via the renin-angiotensin-aldosterone system, critical losses of volume by on the one hand increasing the blood pressure (angiotensin II effect), and on the other hand, by rebalancing the state of filling of the vascular system by increased reabsorption of sodium and water in the kidney (aldosterone effect).

This control system may be pathologically impaired in diverse ways. Thus, a chronic reduction in renal blood flow (e.g. as a result of heart failure and the congestion of blood in the venous system caused thereby) leads to a chronically excessive release of aldosterone. In turn this is followed by an expansion of the blood volume and thereby increases the weakness of the heart through an excessive supply of volume to the heart. Congestion of blood in the lungs with shortness of breath and formation of edema in the extremities, and ascites and pleural effusions may be the result; the renal blood flow falls further. In addition, the excessive aldosterone effect leads to a reduction in the potassium concentration in the blood and in the extracellular fluid. In heart muscles which have been previously damaged otherwise, cardiac arrhythmias with a fatal outcome may be induced if there is a deviation below a critical minimum level. This is likely to be one of the main causes of the sudden cardiac death which frequently occurs in patients with heart failure.

In addition, aldosterone is also thought to be responsible for a number of the myocardial remodeling processes typically to be observed in heart failure. Thus, hyperaldosteronism is a crucial component in the pathogenesis and prognosis of heart failure which may originally be induced by various types of damage such as, for example, a myocardial infarction, a myocardial inflammation or high blood pressure. This assumption is supported by the fact that there was a marked reduction in overall mortality in wide-ranging clinical studies on groups of patients with chronic heart failure and post acute myocardial infarction through the use of aldosterone antagonists [B. Pitt, F. Zannad, W. J. Remme et al., *N. Engl. J. Med.* 341, 709-717 (1999); B. Pitt, W. Remme, F. Zannad et al., *N. Engl. J. Med.* 348, 1309-1321 (2003)]. It was possible to achieve this inter alia by reducing the incidence of sudden cardiac death.

According to recent studies, a not inconsiderable number of patients suffering from essential hypertension are also found to have a so-called normokalemic variant of primary hyperaldosteronism [prevalence up to 11% of all hypertensives: L. Seiler and M. Reincke, *Der Aldosteron-Renin-Quotient bei sekundärer Hypertonie*, Herz 28, 686-691 (2003)]. The best diagnostic method for normokalemic hyperaldosteronism is the aldosterone/renin quotient of the corresponding plasma concentrations, so that relative elevations in aldosterone in relation to the renin plasma concentrations can also be diagnosed and eventually treated. For this reason, a hyperaldosteronism diagnosed in connection with essential hypertension is a starting point for a causal and prophylactically worthwhile therapy.

Far less common than the types of hyperaldosteronism detailed above are pathological states in which the impairment either is to be found in the hormone-producing cells of the adrenal itself, or the number or mass thereof is increased through hyperplasia or proliferation. Adenomas or diffuse hyperplasias of the adrenal cortex are the commonest cause of the primary hyperaldosteronism referred to as Conn's syndrome, the leading symptoms of which are hypertension and hypokalemic alkalosis. The priority here too, besides surgical removal of the diseased tissue, is medical therapy with aldosterone antagonists [H. A. Kühn and J. Schirmeister (Editors), *Innere Medizin,* 4th edition, Springer Verlag, Berlin, 1982].

Another pathological state associated typically with an elevation of the plasma aldosterone concentration is advanced cirrhosis of the liver. The cause of the aldosterone elevation in this case is mainly the restricted aldosterone breakdown resulting from the impairment of liver function. Volume overload, edema and hypokalemia are the typical consequences, which can be successfully alleviated in clinical practice by aldosterone antagonists.

The effects of aldosterone are mediated by the mineralocorticoid receptor which has an intracellular location in the target cells. The aldosterone antagonists available to date have, like aldosterone itself, a basic steroid structure. The utility of such steroidal antagonists is limited by their interactions with the receptors of other steroid hormones, which in some cases lead to considerable side effects such as gynecomastia and impotence and to discontinuation of the therapy [M. A. Zaman, S. Oparil, D. A. Calhoun, *Nature Rev. Drug Disc.* 1, 621-636 (2002)].

The use of potent, non-steroidal antagonists which are more selective for the mineralocorticoid receptor provides the possibility of avoiding this profile of side effects and thus achieving a distinct therapeutic advantage.

The object of the present invention is to provide novel compounds which can be used as selective mineralocorticoid receptor antagonists for the treatment of disorders, especially cardiovascular disorders.

EP 0 133 530-A, EP 0 173 933-A, EP 0 189 898-A and EP 0 234 516-A disclose 4-aryl-substituted 1,4-dihydro-1,6-naphthyridines and -naphthyridinones having a calcium-antagonistic effect for the treatment of vascular disorders. The pharmacological profile of these compounds is reported inter alia in G. Werner et al., *Naunyn-Schmiedeberg's Arch. Pharmacol.* 344 (3), 337-344 (1991). In addition, 1,4-dihydro-1,6-naphthyridine derivatives are claimed in WO 02/10164 as potassium channel openers for the treatment of various, in particular urological, disorders. 4-Fluorenonyl- and 4-chromenonyl-1,4-dihydropyridine derivatives are described as mineralocorticoid receptor antagonists in WO 2005/087740 and WO 2007/009670. WO 2006/066011 discloses 4-aryl-3-cyano-1,4-dihydropyridine-5-carboxylic esters and carboxamides as in some cases dual modulators of steroid hormone receptors and of the L-type calcium channel, and WO 2005/097118 claims compounds having a 4-aryl-1,4-dihydropyridine core structure as aldosterone receptor antagonists.

The present invention relates to compounds of the general formula (I)

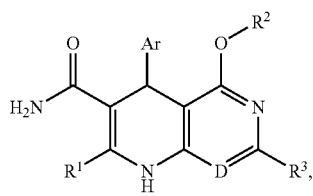

in which
D is N or C—$R^4$, in which
$R^4$ is hydrogen, fluorine, trifluoromethyl or $(C_1-C_4)$-alkyl,
Ar is a group of the formula

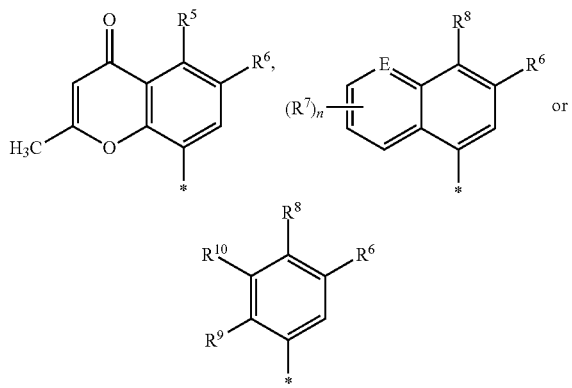

in which
* is the linkage point,
$R^5$ is hydrogen, fluorine, chlorine, cyano, nitro, trifluoromethyl or $(C_1-C_4)$-alkyl,
$R^6$ is hydrogen or fluorine,
$R^7$ is halogen, $(C_1-C_4)$-alkyl, trifluoromethyl, $(C_1-C_4)$-alkoxy or trifluoromethoxy,
$R^8$ is cyano or nitro,
$R^9$ is hydrogen, halogen, $(C_1-C_4)$-alkyl, $(C_1-C_4)$-alkoxy, $(C_1-C_4)$-alkylthio or di-$(C_1-C_4)$-alkylamino, it being possible for the alkyl group in said $(C_1-C_4)$-alkyl, $(C_1-C_4)$-alkoxy and $(C_1-C_4)$-alkylthio radicals in each case to be substituted up to three times by fluorine,
or
phenyl, which may be substituted by halogen, $(C_1-C_4)$-alkyl or trifluoromethyl,
$R^{10}$ is hydrogen, halogen or $(C_1-C_4)$-alkyl,
E is CH, C—$R^7$ or N,
and
n is the number 0, 1 or 2,
it being possible in the case where the substituent $R^7$ occurs more than once for its meanings to be identical or different,
$R^1$ is $(C_1-C_4)$-alkyl which may be substituted up to three times by fluorine,
$R^2$ is $(C_1-C_6)$-alkyl which may be substituted by $(C_3-C_7)$-cycloalkyl or up to three times by fluorine, or is a group of the formula —$SO_2$—$R^{11}$ in which
$R^{11}$ is $(C_1-C_6)$-alkyl, trifluoromethyl, $(C_3-C_7)$-cycloalkyl, phenyl or 5- or 6-membered heteroaryl having up to two heteroatoms from the series N, O and/or S, it being possible for phenyl and heteroaryl in turn each to be substituted once or twice, identically or differently, by halogen, cyano, nitro, $(C_1-C_4)$-alkyl, trifluoromethyl, $(C_1-C_4)$-alkoxy and/or trifluoromethoxy,
and
$R^3$ is hydrogen, fluorine, trifluoromethyl or $(C_1-C_4)$-alkyl,
and the salts, solvates and solvates of the salts thereof.

Compounds of the invention are the compounds of the formula (I) and the salts, solvates and solvates of the salts thereof; the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds of the invention may, depending on their structure, exist in stereoisomeric forms (enantiomers, diastereomers). The present invention therefore relates to the enantiomers or diastereomers and respective mixtures thereof. The stereoisomerically pure constituents can be isolated in a known manner from such mixtures of enantiomers and/or diastereomers.

If the compounds of the invention may occur in tautomeric forms, the present invention encompasses all tautomeric forms.

Salts which are preferred for the purposes of the present invention are physiologically acceptable salts of the compounds of the invention. Also encompassed are salts which are themselves unsuitable for pharmaceutical uses but can be used for example for isolating or purifying the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of the compounds of the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds of the invention (for example by metabolism or hydrolysis).

In the context of the present invention, the substituents have the following meaning, unless specified otherwise:

$(C_1-C_6)$-Alkyl and $(C_1-C_4)$-alkyl represent in the context of the invention a straight-chain or branched alkyl radical having respectively 1 to 6 and 1 to 4 carbon atoms. A straight-chain or branched alkyl radical having 1 to 4 carbon atoms is preferred. Mention may be made by way of example and preferably of: methyl, ethyl, n-propyl, isopropyl, n-butyl, iso-butyl, sec-butyl, tert-butyl, 1-ethylpropyl, n-pentyl, isopentyl and n-hexyl.

$(C_3-C_7)$-Cycloalkyl represents in the context of the invention a saturated monocyclic cycloalkyl group having 3 to 7 carbon atoms. Preference is given to a cycloalkyl radical having 3 to 6 carbon atoms. Mention may be made by way of example and preferably of: cyclopropyl, cyclobutyl, cyclopentyl, cyclohexyl and cycloheptyl.

$(C_1-C_4)$-Alkoxy represents in the context of the invention a straight-chain or branched alkoxy radical having 1 to 4 carbon atoms. Mention may be made by way of example and preferably of: methoxy, ethoxy, n-propoxy, isopropoxy, n-butoxy and tert-butoxy.

$(C_1-C_4)$-Alkylthio represents in the context of the invention a straight-chain or branched alkylthio radical having 1 to 4 carbon atoms. Mention may be made by way of example and preferably of: methylthio, ethylthio, n-propylthio, isopropylthio, n-butylthio and tert-butylthio.

Di-$(C_1-C_4)$-alkylamino represents in the context of the invention an amino group having two identical or different straight-chain or branched alkyl substituents, each of which have 1 to 4 carbon atoms. Mention may be made by way of example and preferably of: N,N-dimethylamino, N,N-diethylamino, N-ethyl-N-methylamino, N-methyl-N-n-propylamino, N,N-diisopropylamino, N-isopropyl-N-n-propylamino, N-n-butyl-N-methylamino and N-tert-butyl-N-methylamino.

5- or 6-membered heteroaryl represents in the context of the invention an aromatic heterocycle (heteroaromatic) having 5 or 6 ring atoms which comprises one or two ring atoms from the series N, O and/or S and is linked via a ring carbon atom. Mention may be made by way of example and preferably of: furyl, pyrrolyl, thienyl, pyrazolyl, imidazolyl, thiazolyl, oxazolyl, isoxazolyl, isothiazolyl, pyridyl, pyrimidinyl, pyridazinyl and pyrazinyl.

Halogen includes in the context of the invention fluorine, chlorine, bromine and iodine. Fluorine or chlorine are preferred.

If radicals in the compounds of the invention are substituted, the radicals may be substituted one or more times, unless specified otherwise. In the context of the present invention, all radicals which occur more than once have a mutually independent meaning. Substitution by one, two or three identical or different substituents is preferred. Substitution by one substituent is very particularly preferred.

Preference is given in the context of the present invention to compounds of the formula (I) in which
D is C—$R^4$ in which
$R^4$ is hydrogen, methyl or trifluoromethyl,
Ar is a group of the formula

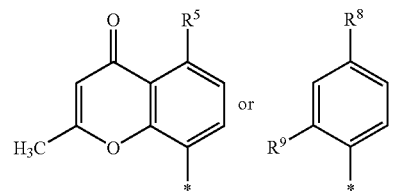

in which
* is the linkage point,
$R^5$ is hydrogen, fluorine, chlorine or cyano,
$R^8$ is cyano or nitro,
and
$R^9$ is chlorine, bromine, $(C_1-C_4)$-alkyl, trifluoromethyl, $(C_1-C_4)$-alkoxy, trifluoromethoxy, $(C_1-C_4)$-alkylthio or trifluoromethylthio,
$R^1$ is methyl or trifluoromethyl,
$R^2$ is $(C_1-C_4)$-alkyl, trifluoromethyl or a group of the formula —$SO_2$—$R^{11}$ in which
$R^{11}$ is $(C_1-C_4)$-alkyl or trifluoromethyl,
and
$R^3$ is hydrogen, methyl or trifluoromethyl,
and the salts, solvates and solvates of the salts thereof.

Particular preference is given in the context of the present invention to compounds of the formula (I) in which
D is C—$R^4$ in which
$R^4$ is hydrogen or methyl,
Ar is a group of the formula

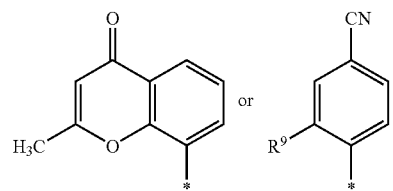

in which
* is the linkage point
and
$R^9$ is ethyl, methoxy or trifluoromethoxy,
$R^1$ is methyl or trifluoromethyl,
$R^2$ is methyl, ethyl, n-propyl or isopropyl
and
$R^3$ is hydrogen or methyl,
and the salts, solvates and solvates of the salts thereof.

Very particular preference is given to compounds of the formula (I) having the following structures:

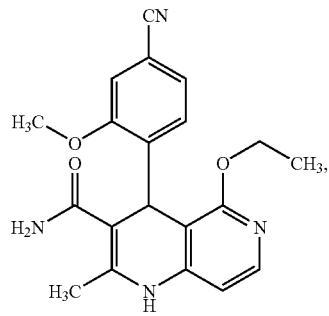

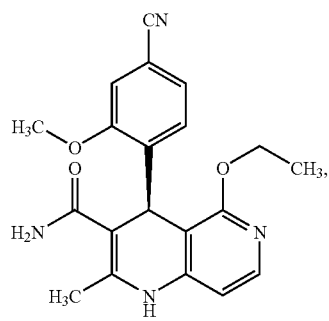

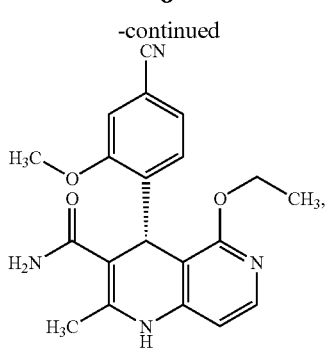

and the salts, solvates and solvates of the salts thereof.

In particular preference is given here to enantiomeric compounds having the following structures:

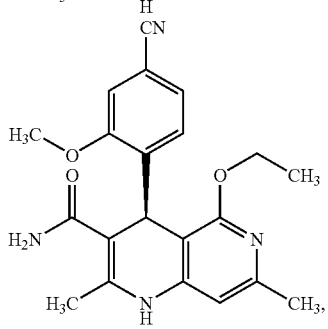

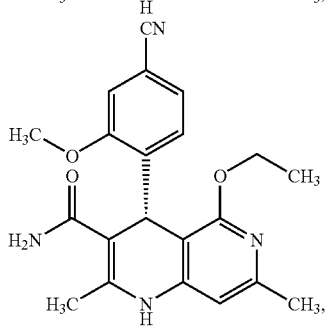

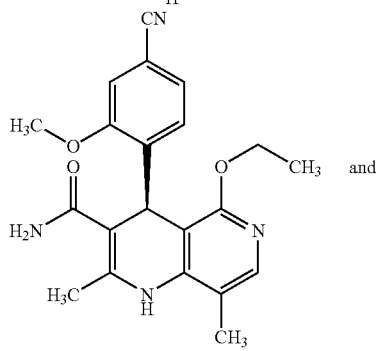

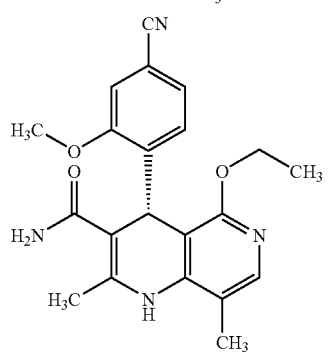

and the salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the invention of the formula (I), characterized in that a compound of the formula (II)

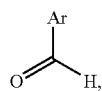
(II)

in which Ar has the meaning indicated above,
is reacted in an inert solvent, where appropriate in the presence of an acid, an acid/base combination and/or a dehydrating agent, with a compound of the formula (III)

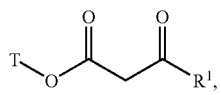
(III)

in which $R^1$ has the meaning indicated above, and
T is allyl or 2-cyanoethyl,
to give a compound of the formula (IV)

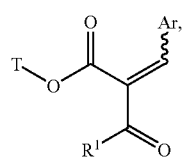
(IV)

in which Ar, T and $R^1$ each have the meanings indicated above,
the latter is then condensed in an inert solvent with a compound of the formula (V)

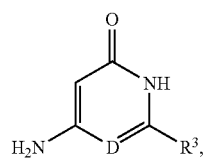
(V)

in which D and $R^3$ have the meanings indicated above,
to give a compound of the formula (VI)

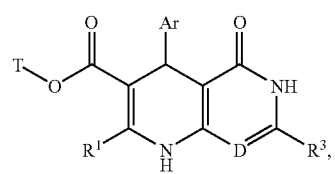
(VI)

in which Ar, D, T, $R^1$ and $R^3$ each have the meanings indicated above,
then the compounds of the formula (VI) are alkylated in an inert solvent, where appropriate in the presence of a base, with a compound of the formula (VII) or a trialkyloxonium salt of the formula (VIII)

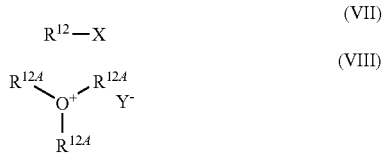

in which
$R^{12}$ is $(C_1-C_6)$-alkyl which may be substituted by $(C_3-C_7)$-cycloalkyl or up to three times by fluorine,
$R^{12A}$ is methyl or ethyl,
X is a leaving group such as, for example, halogen, mesylate, tosylate or triflate,
and
$Y^-$ is a non-nucleophilic anion such as, for example, tetrafluoroborate,
or in the presence of an acid with a trialkyl orthoformate of the formula (IX)

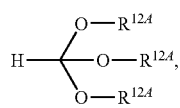
(IX)

in which $R^{12A}$ has the meaning indicated above,
to give compounds of the formula (X-A)

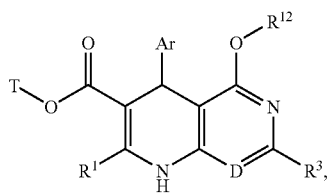
(X-A)

in which Ar, D, T, $R^1$, $R^3$ and $R^{12}$ each have the meanings indicated above,
or the compounds of the formula (VI) are reacted in an inert solvent in the presence of a base with a compound of the formula (XI)

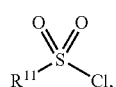
(XI)

in which $R^{11}$ has the meaning indicated above,
to give compounds of the formula (X-B)

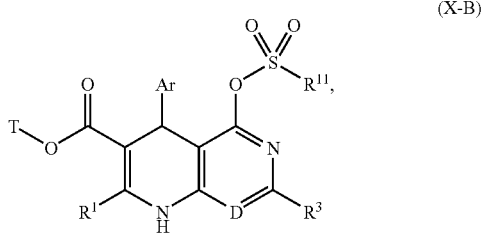

(X-B)

in which Ar, D, T, $R^1$, $R^3$ and $R^{11}$ each have the meanings indicated above,
then the ester group T in the compounds of the formula (X-A) or (X-B) is eliminated by methods known per se to give the carboxylic acids of the formula (XII)

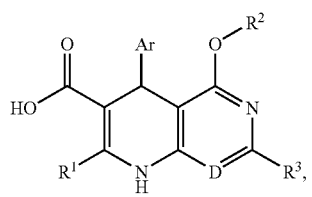

(XII)

in which Ar, D, $R^1$, $R^2$ and $R^3$ each have the meanings indicated above,
then converted with 1,1'-carbonyldiimidazole into the imidazolides of the formula (XIII)

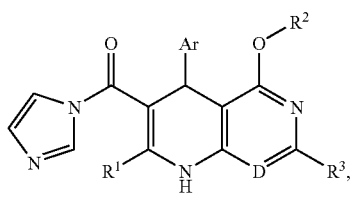

(XIII)

in which Ar, D, $R^1$, $R^2$ and $R^3$ each have the meanings indicated above,
and the latter are then reacted in an inert solvent, where appropriate in the presence of an auxiliary base, with ammonia to give the amides of the formula (I),
and where appropriate the compounds of the formula (I) are separated by methods known to the skilled worker into their enantiomers and/or diastereomers, and/or converted with the appropriate (i) solvents and/or (ii) bases or acids into the solvates, salts and/or solvates of the salts thereof.

The process sequence (II)+(III)→(IV) and (IV)+(V)→(VI) can also be carried out in one stage as 3-component reaction (II)+(III)+(V)→(VI) without isolating the intermediate (IV).

Process steps (II)+(III)→(IV) and (IV)+(V)→(VI) or (II)+(III)+(V)→(VI) are generally carried out in an inert solvent in a temperature range from +20° C. to the boiling point of the solvent under atmospheric pressure.

Inert solvents suitable for this purpose are for example alcohols such as methanol, ethanol, n-propanol, isopropanol, n-butanol or tert-butanol, halohydrocarbons such as dichloromethane, trichloromethane, tetrachloromethane, trichloroethane or 1,2-dichloroethane, or other solvents such as acetonitrile, tetrahydrofuran, dioxane, 1,2-dimethoxyethane, hexane, benzene, toluene, chlorobenzene, pyridine or glacial acetic acid. The reactions are preferably carried out in dichloro-methane, toluene, ethanol or isopropanol at the respective reflux temperature under atmospheric pressure.

Said reactions can where appropriate advantageously take place in the presence of an acid, of an acid/base combination and/or of a dehydrating agent such as, for example, molecular sieves. Examples of suitable acids are acetic acid, trifluoroacetic acid, methanesulfonic acid or p-toluenesulfonic acid; suitable bases are in particular piperidine or pyridine [for the synthesis of 1,4-dihydropyridines, compare also D. M. Stout, A. I. Meyers, *Chem. Rev.* 1982, 82, 223-243; H. Meier et al., *Liebigs Ann. Chem.* 1977, 1888; H. Meier et al., ibid. 1977, 1895; H. Meier et al., ibid. 1976, 1762; F. Bossert et al., *Angew. Chem.* 1981, 93, 755].

Inert solvents for process steps (VI)+(VII)→(X-A), (VI)+(VIII)→(X-A) and (VI)+(XI)→(X-B) are for example ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichloroethane, trichloroethane, tetrachloroethane, trichloroethylene, chlorobenzene or chlorotoluene, or other solvents such as N,N-dimethylformamide (DMF), dimethyl sulfoxide (DMSO), N,N'-dimethylpropyleneurea (DMPU), N-methylpyrrolidone (NMP), pyridine or acetonitrile. It is likewise possible to use mixtures of said solvents. Preference is given to the use of tetrahydrofuran or dimethylformamide in process step (VI)+(VII)→(X-A), of dichloromethane in process step (VI)+(VIII)→(X-A), and of pyridine in process step (VI)+(XI)→(X-B).

Process variant (VI)+(IX)→(X-A) is preferably carried out with a large excess of orthoformic ester in dimethylformamide or without addition of a further solvent; strong inorganic acids such as sulfuric acid for example are advantageous as reaction catalyst [compare for example I. I. Barabanov et al., *Russ. Chem. Bl.* 47 (11), 2256-2261 (1998)].

Bases suitable for process step (VI)+(VII)→(X-A) are in particular alkali metal or alkaline earth metal carbonates such as lithium, sodium, potassium, calcium or cesium carbonate, alkali metal hydrides such as sodium or potassium hydride, amides such as lithium, sodium or potassium bis(trimethylsilyl)amide or lithium diisopropylamide, organometallic compounds such as butyllithium or phenyllithium, or else phosphazene bases such as, for example, P2-t-Bu or P4-t-Bu [so-called "Schwesinger bases", compare R. Schwesinger, H. Schlemper, *Angew. Chem. Int. Ed. Engl.* 26, 1167 (1987); T. Pietzonka, D. Seebach, *Chem. Ber.* 124, 1837 (1991)]. Sodium hydride or the phosphazene base P4-t-Bu is preferably used.

Bases suitable for process step (VI)+(XI)→(X-B) are in particular alkali metal or alkaline earth metal carbonates such as lithium, sodium, potassium, calcium or cesium carbonate, alkali metal hydrides such as sodium or potassium hydride, organometallic compounds such as butyllithium or phenyllithium, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo-[5.4.0]undec-7-ene (DBU) or 1,4-diazabicycl [2.2.2]octane (DABCO®). Pyridine is preferably used and simultaneously also serves as solvent.

Process step (VI)+(VIII)→(X-A) is generally carried out without addition of a base.

The reactions (VI)+(VII)→(X-A), (VI)+(VIII)→(X-A) and (VI)+(XI)→(X-B) generally take place in a temperature range from −20° C. to +100° C., preferably at 0° C. to +60° C.;

process variant (VI)+(IX)→(X-A) is ordinarily carried out in a temperature range from +100° C. to +150° C. The reactions can be carried out under atmospheric, elevated or reduced pressure (e.g. from 0.5 to 5 bar); they are generally carried out under atmospheric pressure.

Elimination of the allyl or 2-cyanoethyl ester in process step (X-A) or (X-B)→(XII) takes place by known methods customary in the literature. In the case of the 2-cyanoethyl ester, an aqueous solution of an alkali metal hydroxide such as, for example, sodium or potassium hydroxide solution is preferably employed for this purpose. The reaction is generally carried out using a water-miscible inert cosolvent such as, for example, tetrahydrofuran, dioxane or 1,2-dimethoxyethane, in a temperature range from 0° C. to +40° C. In the case of the allyl ester, the elimination preferably takes place with the aid of Wilkinson's catalyst [tris(triphenylphosphine) rhodium(I) chloride] in a water/alcohol/acetic acid mixture at temperatures from +50° C. to +100° C. [compare for example Moseley, J. D., *Tetrahedron Lett.* 46, 3179-3181 (2005)].

Examples of inert solvents suitable for process step (XII)→(XIII) are ethers such as diethyl ether, methyl tert-butyl ether, dioxane, tetrahydrofuran, glycol dimethyl ether or diethylene glycol dimethyl ether, halohydrocarbons such as dichloromethane, trichloromethane, 1,2-dichloroethane, trichloroethane, tetrachloroethane, chlorobenzene or chlorotoluene, or other solvents such as N,N-dimethylformamide (DMF), dimethyl sulfoxide (DMSO), N,N'-dimethylpropyleneurea (DMPU), N-methylpyrrolidone (NMP), acetone, acetonitrile or ethyl acetate. It is likewise possible to use mixtures of said solvents. Tetrahydrofuran, dimethylformamide or ethyl acetate is preferably employed. The reaction is ordinarily carried out in a temperature range from 0° to +40° C.

Inert solvents suitable for process step (XIII)→(I) are for example alcohols such as methanol, ethanol, n-propanol, isopropanol, n-butanol or tert-butanol, ethers such as diethyl ether, methyl tert-butyl ether, dioxane, tetrahydrofuran, glycol dimethyl ether or diethylene glycol dimethyl ether, or other solvents such as N,N-dimethylformamide (DMF), dimethyl sulfoxide (DMSO), N,N'-dimethylpropyleneurea (DMPU), N-methylpyrrolidone (NMP), acetonitrile or else water. It is likewise possible to use mixtures of these solvents. Tetrahydrofuran or dimethylformamide is preferably employed.

Suitable as source of ammonia for this reaction are solutions of gaseous ammonia in one of the abovementioned solvents, especially in water. The reaction can where appropriate advantageously be carried out in the presence of a tertiary amine as auxiliary base, such as, for example, triethylamine, N-methylmorpholine, N-methylpiperidine, N,N-diisopropylethylamine or 4-N,N-dimethylaminopyridine. The reaction generally takes place in a temperature range from +20° C. to +120° C., preferably at +50° C. to +100° C.

The compounds of the formula (II) are commercially available, known from the literature or can be prepared in analogy to processes known from the literature (compare reaction schemes 1-7 hereinafter). The compounds of the formulae (III), (VII), (VIII), (IX) and (XI) are in many cases commercially available, known from the literature or can be prepared by methods known from the literature.

The compounds of the formula (V) are described in the literature or can be obtained in analogy to processes known from the literature [compare for example T. Searls, L. W. McLaughlin, *Tetrahedron* 55, 11985-11996 (1999); D. McNamara, P. D. Cook, *J. Med. Chem.* 30, 340-347 (1987); S, Nesnow, C. Heidelberger, *J. Heterocycl. Chem.* 12, 941-944 (1975); N. C. Hung, E. Bisagni, *Synthesis* 1984, 765-766; Z. Foldi et al., *Chem. Ber.* 75 (7), 755-763 (1942); G. W. Kenner et al., *J. Chem. Soc.,* 388 (1943)].

It is possible where appropriate for separation of the enantiomers and/or diastereomers to take place at the stage of the intermediates (VI), (X-A), (X-B) or (XII), which are then subjected separately to the subsequent reactions.

Preparation of the Compounds of the Invention can be Illustrated by the Following Synthesis Schemes:

Scheme 1

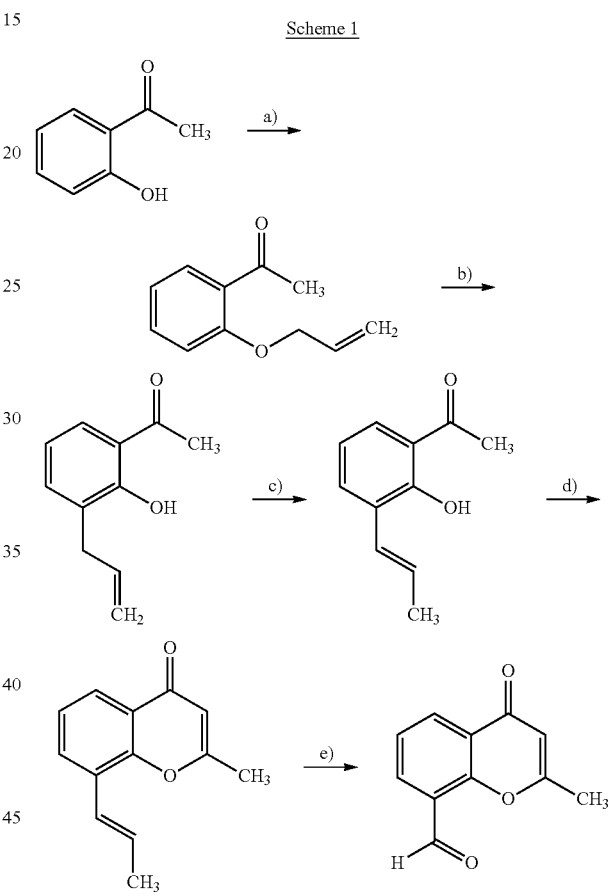

[a]: allyl bromide, potassium carbonate, cat. potassium iodide, acetone, reflux; b): 230° C., 4 h; c): bis(benzonitrile)dichloropalladium(II), toluene, 120° C., 16 h; d): acetyl chloride, sodium hydride, THF, 10-25° C., 16 h; e): 1. ozone, dichloromethane, -60° C., 30 min; 2. dimethyl sulfide].

Scheme 2

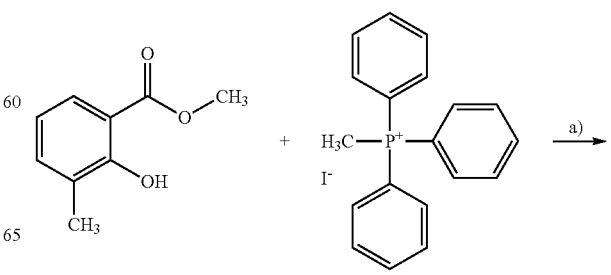

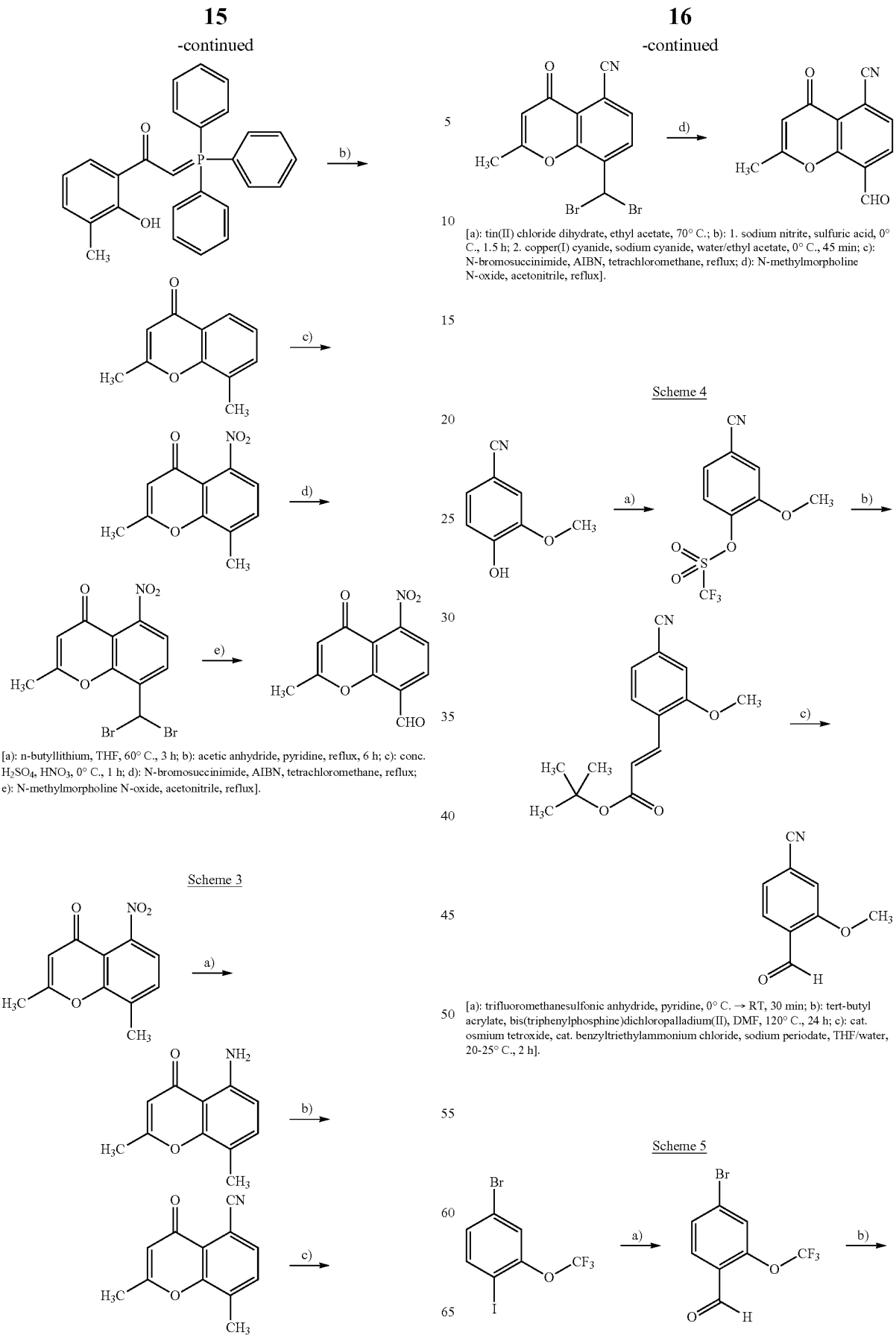

-continued

[a]: n-butyllithium, THF, −78° C., then N-formylmorpholine, b): zinc cyanide, tetrakis(triphenylphosphine)palladium(0), DMF, microwave 250° C./5 min].

Scheme 6

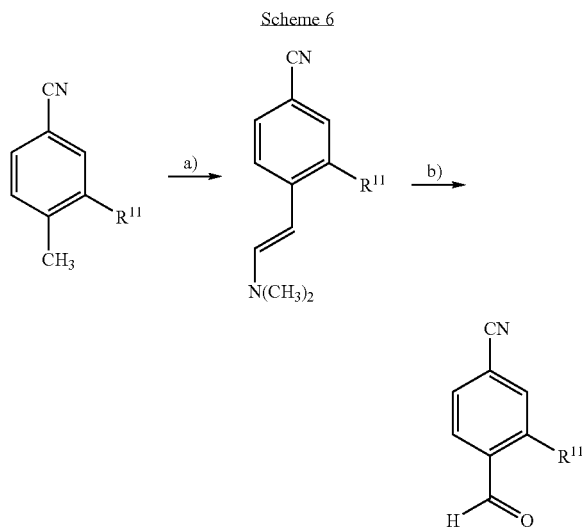

[a]: N,N-dimethylformamide dimethyl acetal, DMF, 140-180° C.; b): sodium periodate, THF/water].

Scheme 7

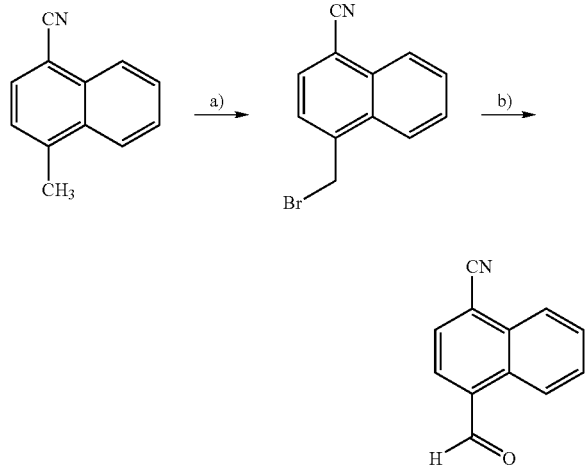

[a]: N-bromosuccinimide, AIBN, tetrachloromethane, reflux; b): N-methylmorpholine N-oxide, acetonitrile, 3 Å molecular sieves].

Scheme 8

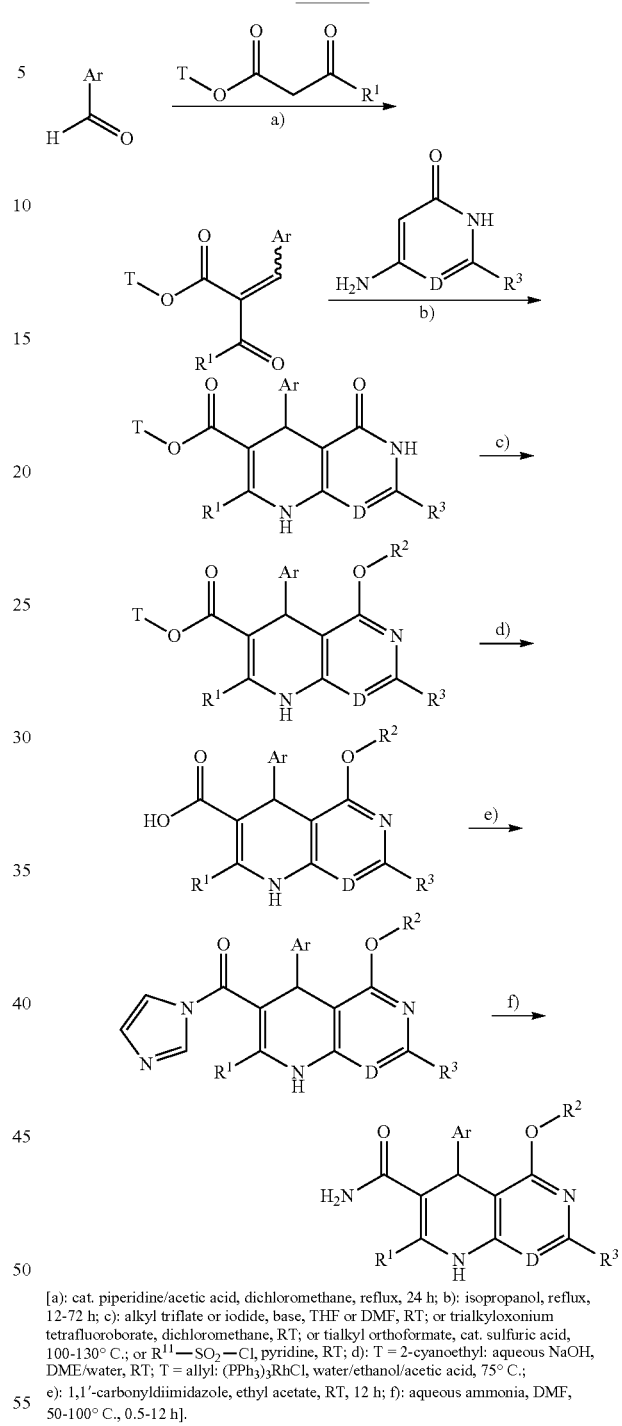

[a]: cat. piperidine/acetic acid, dichloromethane, reflux, 24 h; b): isopropanol, reflux, 12-72 h; c): alkyl triflate or iodide, base, THF or DMF, RT; or trialkyloxonium tetrafluoroborate, dichloromethane, RT; or tialkyl orthoformate, cat. sulfuric acid, 100-130° C.; or $R^{11}$—$SO_2$—Cl, pyridine, RT; d): T = 2-cyanoethyl: aqueous NaOH, DME/water, RT; T = allyl: (PPh$_3$)$_3$RhCl, water/ethanol/acetic acid, 75° C.; e): 1,1′-carbonyldiimidazole, ethyl acetate, RT, 12 h; f): aqueous ammonia, DMF, 50-100° C., 0.5-12 h].

The compounds of the invention act as antagonists of the mineralocorticoid receptor and show a valuable range of pharmacological effects which could not have been predicted. They are therefore suitable for use as medicaments for the treatment and/or prophylaxis of diseases in humans and animals.

The compounds of the invention are suitable for the prophylaxis and/or treatment of various disorders and disease-related conditions, especially of disorders which are characterized either by an elevation of the plasma aldosterone concentration or by a change in the plasma aldosterone concentration relative to the plasma renin concentration, or are associated with these changes. Examples which may be mentioned are: idiopathic primary hyperaldosteronism, hyperaldosteronism associated with adrenal hyperplasia, adrenal adenomas and/or adrenal carcinomas, hyperaldosteronism associated with cirrhosis of the liver, hyperaldosteronism associated with heart failure, and (relative) hyperaldosteronism associated with essential hypertension.

The compounds of the invention are also suitable, because of their mechanism of action, for the prophylaxis of sudden cardiac death in patients at increased risk of dying of sudden cardiac death. These are in particular patients suffering for example from one of the following disorders: primary and secondary hypertension, hypertensive heart disease with or without congestive heart failure, therapy-resistant hypertension, acute and chronic heart failure, coronary heart disease, stable and unstable angina pectoris, myocardial ischemia, myocardial infarction, dilated cardiomyopathies, congenital primary cardiomyopathies such as, for example, Brugada syndrome, cardiomyopathies induced by Chagas' disease, shock, arteriosclerosis, atrial and ventricular arrhythmia, transient and ischemic attacks, stroke, inflammatory cardiovascular disorders, peripheral and cardiac vascular disorders, peripheral blood flow disturbances, arterial occlusive diseases such as intermittent claudication, asymptomatic left-ventricular dysfunction, myocarditis, hypertrophic alterations of the heart, pulmonary hypertension, spasms of the coronary arteries and peripheral arteries, thromboses, thromboembolic disorders, and vasculitis.

The compounds of the invention can additionally be used for the prophylaxis and/or treatment of edema formation, such as, for example, pulmonary edema, renal edema or heart failure-related edema, and of restenoses such as following thrombolysis therapies, percutaneous transluminal angioplasties (PTA) and coronary angioplasties (PTCA), heart transplants and bypass operations.

The compounds of the invention are further suitable for use as potassium-sparing diuretic and for electrolyte disturbances such as, for example, hypercalcemia, hypernatremia or hypokalemia.

The compounds of the invention are likewise suitable for the treatment of renal disorders such as acute and chronic renal failure, hypertensive kidney disease, arteriosclerotic nephritis (chronic and interstitial), nephrosclerosis, chronic renal failure and cystic renal disorders, for the prevention of kidney damage which may be caused for example by immunosuppressants such as cyclosporin A in association with organ transplants, and for renal cancer.

The compounds of the invention can additionally be employed for the prophylaxis and/or treatment of diabetes mellitus and diabetic sequelae such as, for example, neuropathy and nephropathy.

The compounds of the invention can further be used for the prophylaxis and/or treatment of microalbuminuria, for example caused by diabetes mellitus or high blood pressure, and of proteinuria.

The compounds of the invention are also suitable for the prophylaxis and/or treatment of disorders associated either with an increase in the plasma glucocorticoid concentration or with a local increase in the concentration of glucocorticoids in tissue (e.g. of the heart). Examples which may be mentioned are: adrenal dysfunctions leading to overproduction of glucocorticoids (Cushing's syndrome), adrenocortical tumors with resulting overproduction of glucocorticoids, and pituitary tumors which autonomously produce ACTH (adrenocorticotropic hormone) and thus lead to adrenal hyperplasias with resulting Cushing's disease.

The compounds of the invention can additionally be employed for the prophylaxis and/or treatment of obesity, of metabolic syndrome and of obstructive sleep apnea.

The compounds of the invention can further be used for the prophylaxis and/or treatment of inflammatory disorders caused for example by viruses, spirochetes, fungi, bacteria or mycobacteria, and of inflammatory disorders of unknown etiology, such as polyarthritis, lupus erythematosus, peri- or polyarteritis, dermatomyositis, scleroderma and sarcoidosis.

The compounds of the invention can further be employed for the treatment of central nervous disorders such as depressions, anxiety states and chronic pain, especially migraine, and for neurodegenerative disorders such as Alzheimer's disease and Parkinson's syndrome.

The compounds of the invention are also suitable for the prophylaxis and/or treatment of vascular damage, e.g. following procedures such as percutaneous transluminal coronary angioplasty (PTCA), implantations of stents, coronary angioscopy, reocclusion or restenosis following bypass operations, and for endothelial dysfunction, for Raynaud's disease, for thromboangiitis obliterans (Buerger's syndrome) and for tinnitus syndrome.

The present invention further relates to the use of the compounds of the invention for the treatment and/or prevention of disorders, especially of the aforementioned disorders.

The present invention further relates to the use of the compounds of the invention for the manufacture of a medicament for the treatment and/or prevention of disorders, especially of the aforementioned disorders.

The present invention further relates to a method for the treatment and/or prevention of disorders, especially of the aforementioned disorders, by using an effective amount of at least one of the compounds of the invention.

The compounds of the invention can be employed alone or, if required, in combination with other active ingredients. The present invention further relates to medicaments comprising at least one of the compounds of the invention and one or more further active ingredients, especially for the treatment and/or prevention of the aforementioned disorders. Suitable active ingredients for combinations are by way of example and preferably:

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers and Rho kinase inhibitors;

diuretics, especially loop diuretics, and thiazides and thiazide-like diuretics;

agents having an antithrombotic effect, for example and preferably from the group of platelet aggregation inhibitors, of anticoagulants or of profibrinolytic substances;

active ingredients which alter lipid metabolism, for example and preferably from the group of thyroid receptor agonists, cholesterol synthesis inhibitors such as by way of example and preferably HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile adsorbents, bile acid reabsorption inhibitors and lipoprotein(a) antagonists;

organic nitrates and NO donors such as, for example, sodium nitroprusside, nitroglycerin, isosorbide mononitrate, isosorbide dinitrate, molsidomine or SIN-1, and inhaled NO;

compounds having a positive inotropic effect, such as, for example, cardiac glycosides (digoxin), beta-adrenergic and dopaminergic agonists such as isoproterenol, adrenaline, noradrenaline, dopamine and dobutamine;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, especially PDE 5 inhibitors such as sildenafil, vardenafil and tadalafil, and PDE 3 inhibitors such as aminone and milrinone;

natriuretic peptides such as, for example, atrial natriuretic peptide (ANP, anaritide), B-type natriuretic peptide or brain natriuretic peptide (BNP, nesiritide), C-type natriuretic peptide (CNP) and urodilatin;

calcium sensitizers such as by way of example and preferably levosimendan;

NO-independent but heme-dependent stimulators of guanylate cyclase such as in particular the compounds described in WO 00/06568, WO 00/06569, WO 02/42301 and WO 03/095451;

NO- and heme-independent activators of guanylate cyclase, such as in particular the compounds described in WO 01/19355, WO 01/19776, WO 01/19778, WO 01/19780, WO 02/070462 and WO 02/070510;

inhibitors of human neutrophil elastase (HNE), such as, for example, sivelestat or DX-890 (reltran);

compounds which inhibit the signal transduction cascade, such as, for example, tyrosine kinase inhibitors, in particular sorafenib, imatinib, gefitinib and erlotinib; and/or compounds which influence the energy metabolism of the heart, such as by way of example and preferably etomoxir, dichloroacetate, ranolazine or trimetazidine.

In a preferred embodiment of the invention, the compounds of the invention are administered in combination with a diuretic such as by way of example and preferably furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorophenamide, methazolamide, glycerol, isosorbide, mannitol, amiloride or triamterene.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, Rho kinase inhibitors, and diuretics.

In a preferred embodiment of the invention, the compounds of the invention are administered in combination with a calcium antagonist such as by way of example and preferably nifedipine, amlodipine, verapamil or diltiazem.

In a preferred embodiment of the invention, the compounds of the invention are administered in combination with an angiotensin AII antagonist such as by way of example and preferably losartan, candesartan, valsartan, telmisartan or embusartan.

In a preferred embodiment of the invention, the compounds of the invention are administered in combination with an ACE inhibitor such as by way of example and preferably enalapril, captopril, lisinopril, ramipril, delapril, fosinopril, quinopril, perindopril or trandopril.

In a preferred embodiment of the invention, the compounds of the invention are administered in combination with an endothelin antagonist such as by way of example and preferably bosentan, darusentan, ambrisentan or sitaxsentan.

In a preferred embodiment of the invention, the compounds of the invention are administered in combination with a renin inhibitor such as by way of example and preferably aliskiren, SPP-600, SPP-635, SPP-676, SPP-800 or SPP-1148.

In a preferred embodiment of the invention, the compounds of the invention are administered in combination with an alpha-1 receptor blocker such as by way of example and preferably prazosin.

In a preferred embodiment of the invention, the compounds of the invention are administered in combination with a beta-receptor blocker such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with a Rho kinase inhibitor such as by way of example and preferably fasudil, Y-27632, SLx-2119, BF-66851, BF-66852, BF-66853, KI-23095 or BA-1049.

Agents having an antithrombotic effect (antithrombotics) preferably mean compounds from the group of platelet aggregation inhibitors, of anticoagulants or of profibrinolytic substances.

In a preferred embodiment of the invention, the compounds of the invention are administered in combination with a platelet aggregation inhibitor such as by way of example and preferably aspirin, clopidogrel, ticlopidine or dipyridamole.

In a preferred embodiment of the invention, the compounds of the invention are administered in combination with a thrombin inhibitor such as by way of example and preferably ximelagatran, melagatran, bivalirudin or clexane.

In a preferred embodiment of the invention, the compounds of the invention are administered in combination with a GPIIb/IIIa antagonist such as by way of example and preferably tirofiban or abciximab.

In a preferred embodiment of the invention, the compounds of the invention are administered in combination with a factor Xa inhibitor such as by way of example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or a low molecular weight (LMW) heparin derivative.

In a preferred embodiment of the invention, the compounds of the invention are administered in combination with a vitamin K antagonist such as by way of example and preferably coumarin.

Agents which alter lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds of the invention are administered in combination with a CETP inhibitor such as by way of example and preferably torcetrapib (CP-529 414), JJT-705, BAY 60-5521, BAY 78-7499 or CETP vaccine (Avant).

In a preferred embodiment of the invention, the compounds of the invention are administered in combination with a thyroid receptor agonist such as by way of example and preferably D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins such as by way of example and preferably lovastatin, simvastatin, pravastatin, fluvastatin, atorvastatin, rosuvastatin, cerivastatin or pitavastatin.

In a preferred embodiment of the invention, the compounds of the invention are administered in combination with a squalene synthesis inhibitor such as by way of example and preferably BMS-188494 or TAK-475.

In a preferred embodiment of the invention, the compounds of the invention are administered in combination with an ACAT inhibitor such as by way of example and preferably avasimibe, melinamide, pactimibe, eflucimibe or SMP-797.

In a preferred embodiment of the invention, the compounds of the invention are administered in combination with an MTP inhibitor such as by way of example and preferably implitapide, BMS-201038, R-103757 or JTT-130.

In a preferred embodiment of the invention, the compounds of the invention are administered in combination with a PPAR-gamma agonist such as by way of example and preferably pioglitazone or rosiglitazone.

In a preferred embodiment of the invention, the compounds of the invention are administered in combination with a PPAR-delta agonist such as by way of example and preferably GW-501516 or BAY 68-5042.

In a preferred embodiment of the invention, the compounds of the invention are administered in combination with a cholesterol absorption inhibitor such as by way of example and preferably ezetimibe, tiqueside or pamaqueside.

In a preferred embodiment of the invention, the compounds of the invention are administered in combination with a lipase inhibitor such as by way of example and preferably orlistat.

In a preferred embodiment of the invention, the compounds of the invention are administered in combination with a polymeric bile adsorbent such as by way of example and preferably cholestyramine, colestipol, colesolvam, CholestaGel or colestimide.

In a preferred embodiment of the invention, the compounds of the invention are administered in combination with a bile acid reabsorption inhibitor such as by way of example and preferably ASBT (=IBAT) inhibitors such as, for example, AZD-7806, S-8921, AK-105, BARI-1741, SC-435 or SC-635.

In a preferred embodiment of the invention, the compounds of the invention are administered in combination with a lipoprotein(a) antagonist such as by way of example and preferably gemcabene calcium (CI-1027) or nicotinic acid.

The present invention further relates to medicaments which comprise at least one compound of the invention, normally together with one or more inert, non-toxic, pharmaceutically suitable excipients, and to the use thereof for the aforementioned purposes.

The compounds of the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds of the invention can be administered in administration forms suitable for these administration routes.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated and coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral or parenteral administration are preferred, especially oral and intravenous administration.

The compounds of the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorings (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight per day to achieve effective results. On oral administration, the dosage is about 0.01 to 100 mg/kg, preferably about 0.01 to 20 mg/kg, and very particularly preferably about 0.1 to 10 mg/kg of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

A. EXAMPLES

| Abbreviations and acronyms: | |
|---|---|
| abs. | absolute |
| AIBN | 2,2'-azobis-2-methylpropanenitrile |
| aq. | aqueous, aqueous solution |
| cat. | catalytic |
| CI | chemical ionization (in MS) |
| conc. | concentrated |
| d | day(s) |
| DME | 1,2-dimethoxyethane |
| DMF | dimethylformamide |
| DMSO | dimethyl sulfoxide |
| ee | enantiomeric excess |
| EI | electron impact ionization (in MS) |
| ent | enantiomer/enantiopure |
| eq | equivalent(s) |
| ESI | electrospray ionization (in MS) |
| GC-MS | coupled gas chromatography-mass spectrometry |
| h | hour(s) |
| HPLC | high pressure, high performance liquid chromatography |
| LC-MS | coupled liquid chromatography-mass spectrometry |
| min | minute(s) |
| MPLC | medium pressure liquid chromatography |
| MS | mass spectrometry |
| NMR | nuclear magnetic resonance spectrometry |
| Ph | phenyl |
| $R_f$ | retention index (in TLC) |
| $R_t$ | retention time (in HPLC) |
| RT | room temperature |
| THF | tetrahydrofuran |
| TLC | thin-layer chromatography |
| v/v | volume-to-volume ratio (of a solution) |
| wt % | percent by weight |

LC-MS and GC-MS Methods:

Method 1 (LC-MS):

MS instrument type: Micromass ZQ; HPLC instrument type: Waters Alliance 2795; column: Phenomenex Synergi 2μ, Hydro-RP Mercury 20 mm×4 mm; eluent A: 1 l of water+0.5 ml of 50% formic acid, eluent B: 1 l of acetonitrile+0.5 ml of 50% formic acid; gradient 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm Method 2 (LC-MS):

Instrument: Micromass Quattro LCZ with HPLC Agilent Series 1100; column: Phenomenex Synergi 2μ, Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm Method 3 (LC-MS):

MS instrument type: Micromass ZQ; HPLC instrument type: HP 1100 Series; UV DAD; column: Phenomenex Gemini 3μ, 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm Method 4 (LC-MS):

Instrument: Micromass Platform LCZ with HPLC Agilent Series 1100; column: Thermo Hypersil GOLD 3μ, 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 5 (GC-MS):

Instrument: Micromass GCT, GC 6890; column: Restek RTX-35MS, 30 m×250 μm×0.25 μm; constant flow with helium: 0.88 ml/min; oven: 60° C.; inlet: 250° C.; gradient: 60° C. (halt for 0.30 min), 50° C./min→120° C., 16° C./min→250° C., 30° C./min→300° C. (halt for 1.7 min).

Method 6 (LC-MS):

MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient 0.0 min 90% A→2 min 65% A→4.5 min 5% A→6 min 5% A; flow rate: 2 ml/min; oven: 40° C.; UV detection: 210 nm Method 7 (LC-MS):

Instrument: Micromass Quattro LCZ with HPLC Agilent Series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm Method 8 (LC-MS):

Instrument type: Micromass ZQ; instrument type: Waters Alliance 2795: column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient 0.0 min 90% A→0.1 min 90% A→3.0 min 5% A→4.0 min 5% A→4.01 min 90% A; flow: 2 ml/min; oven: 50° C.; UV detection: 210 nm Method 9 (LC-MS):

Instrument: Micromass Quattro Premier with Waters HPLC Acquity; column: Thermo Hypersil GOLD 1.9μ, 50 nm×1 nm; eluent A: 1 l water+0.5 ml 50% formic acid, eluent B: 1 l acetonitrile+0.5 ml 50% formic acid; gradient: 0.0 min 90% A→0.1 min 90% A→1.5 min 10% A→2.2 min 10% A; flow 0.33 ml/min; oven: 50° C.; UV detection: 210 nm.

Starting Compounds and Intermediates

Example 1A

1-[2-(allyloxy)phenyl]ethanone

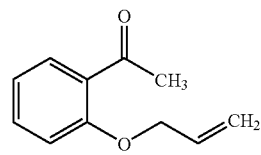

542 g (3.9 mol) of 2-hydroxyacetophenone are heated to reflux with 592 g (4.9 mol) of allyl bromide, 1000 g (7.2 mol) of potassium carbonate and 13.2 g (79 mmol) of potassium iodide in 2.4 liters of acetone for 24 h. Cooling to room temperature is followed by filtration, and the solvent is removed in vacuo. The residue is dissolved in toluene and washed with 10% strength sodium hydroxide solution and water. Concentration results in 689 g (98% of theory) of the title compound.

$^1$H-NMR (300 MHz, CDCl$_3$): δ=2.68 (s, 3H), 4.68 (dd, 2H), 5.89 (dd, 2H), 6.09 (m, 1H), 6.99 (dd, 2H), 7.44 (m, 1H), 7.71 (d, 1H).

Example 2A 1-(3-allyl-2-hydroxyphenyl)ethanone

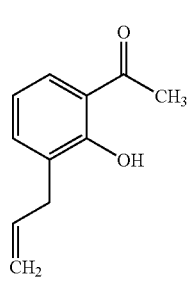

160 g (0.9 mol) of 1-[2-(allyloxy)phenyl]ethanone are stirred in a metal bath at 230-240° C. for 4 h. After cooling to room temperature, the product is distilled in a thin-film evaporator at 140° C. and 0.4 mbar. 155 g (97% of theory) of the title compound are obtained.

$^1$H-NMR (300 MHz, CDCl$_3$): δ=2.68 (s, 3H), 3.44 (d, 2H), 5.09 (m, 2H), 6.01 (m, 1H), 6.85 (t, 1H), 7.38 (dd, 1H), 7.62 (dd, 1H), 12.61 (s, 1H).

Example 3A

1-{2-Hydroxy-3-[(1E)-prop-1-en-1-yl]phenyl}ethanone

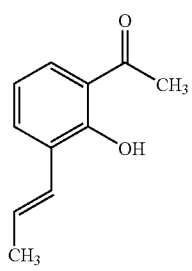

40 g (227 mmol) of 1-(3-allyl-2-hydroxyphenyl)ethanone are dissolved in 120 ml of toluene, and 2.17 g (5.6 mmol) of bis(benzonitrile)dichloropalladium(II) are added. The reaction mixture is heated at 120° C. overnight. Cooling to room temperature is followed by filtration through kieselguhr, and the solvent is removed in vacuo. 20.9 g (95% of theory) of the title compound are obtained and are reacted without further purification in the next stage.

LC-MS (method 1): R$_t$=2.36 min; [M+H]$^+$=177

$^1$H-NMR (300 MHz, CDCl$_3$): δ=1.91 (dd, 3H), 2.63 (s, 3H), 6.32 (m, 1H), 6.73 (dd, 1H), 6.85 (t, 1H), 7.59 (m, 2H), 12.74 (s, 1H).

Example 4A

2-Methyl-8-[(1E)-prop-1-en-1-yl]-4H-chromen-4-one

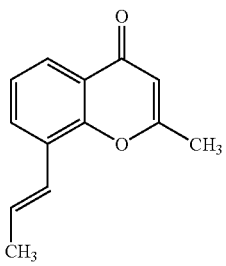

12.52 g (313.2 mmol) of 60% sodium hydride (suspension in mineral oil) are introduced into 300 ml of absolute THF under argon at 10° C. 18.4 g (104.4 mmol) of 1-{2-hydroxy-3-[(1E)-prop-1-en-1-yl]phenyl}ethanone are slowly added dropwise to the suspension. After 15 min, 9 g (114.9 mmol) of acetyl chloride are added. The reaction mixture is stirred at room temperature overnight. Hydrolysis is carried out with 300 ml of water, and the mixture is extracted several times with ethylacetate. Washing of the organic phase with saturated sodium chloride solution is followed by drying over sodium sulfate. The solvent is then removed in vacuo. The residue is taken up in 200 ml of methanol and heated with 50 ml of 20% strength hydrochloric acid at 80° C. for 30 min. The solvent is then removed in vacuo, and the residue is mixed with 400 ml of water. Several extractions with dichloromethane are carried out. After the organic phase has been dried over magnesium sulfate, the solvent is removed in vacuo and the residue is purified by column chromatography (mobile phase: dichloromethane/methanol 98:2). 10.5 g (50.2% of theory) of the title compound are obtained as a yellow oil.

LC-MS (method 2): R$_t$=2.07 min; [M+H]$^+$=201

$^1$H-NMR (300 MHz, CDCl$_3$): δ=1.98 (dd, 3H), 2.43 (s, 3H), 6.18 (s, 1H), 6.40 (m, 1H), 6.85 (dd, 1H), 7.31 (t, 1H), 7.72 (dd, 1H), 8.05 (dd, 1H).

Example 5A

2-Methyl-4-oxo-4H-chromene-8-carbaldehyde

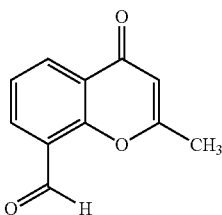

18.5 g (62.8 mmol) of 2-methyl-8-[(1E)-prop-1-en-1-yl]-4H-chromen-4-one are dissolved in 400 ml of dichloromethane and cooled to −60° C. Ozone is passed into the reaction solution for 30 min Dimethyl sulfide is then added to the reaction mixture. After warming to room temperature, the solvent is removed in vacuo and the residue is slurried in a little methanol. The solid remaining after filtration is recrystallized from diethyl ether. 9.1 g (77.4% of theory) of the title compound are obtained.

LC-MS (method 1): $R_t$=1.31 min; [M+H]$^+$=189

$^1$H-NMR (300 MHz, CDCl$_3$): δ=2.48 (s, 3H), 6.27 (s, 1H), 7.51 (m, 1H), 8.21 (dd, 1H), 8.46 (dd, 1H), 10.67 (s, 1H).

Example 6A

4-Bromo-2-(trifluoromethoxy)benzaldehyde

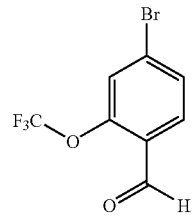 [SMILES: O=Cc1ccc(Br)cc1OC(F)(F)F]

20.00 g (54.51 mmol) of 4-bromo-2-(trifluoromethoxy)iodobenzene are dissolved in 200 ml of THF and cooled to −78° C. Then 26.16 ml (65.41 mmol) of a 2.5 M solution of n-butyllithium in hexane are added dropwise. The mixture is stirred for 30 min and then 14.43 g (125.37 mmol) of N-formylmorpholine are metered in. After complete conversion is detected (TLC check), solvolysis is carried out at −78° C. with isopropanol. Warming to room temperature is followed by addition of water and extraction twice with dichloromethane. The combined organic phases are washed with saturated sodium chloride solution and dried with sodium sulfate, and the solvent is distilled out under reduced pressure. The residue is purified by column chromatography (silica gel, mobile phase: cyclohexane/ethyl acetate 5:1). 11.43 g (78% of theory) of the title compound are obtained.

GC-MS (method 5): $R_t$=4.24 min; MS (EIpos): m/z=270 [M+H]$^+$ $^1$H-NMR (300 MHz, DMSO-d$_6$): δ=7.85-7.92 (m, 3H), 10.20 (s, 1H).

Example 7A

4-Formyl-3-(trifluoromethoxy)benzonitrile

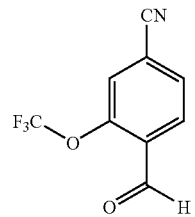 [SMILES: N#Cc1ccc(C=O)c(OC(F)(F)F)c1]

10.63 g (39.51 mmol) of 4-bromo-2-(trifluoromethoxy)benzaldehyde, 3.43 g (29.24 mmol) of zinc cyanide and 1.37 g (1.19 mmol) of tetrakis(triphenylphosphine)palladium(0) are dissolved in 80 ml of DMF. The reaction mixture is then reacted in several portions in a single mode microwave (Emrys Optimizer, 5 min at 220° C.). The combined mixtures are mixed with water and extracted twice with toluene. The combined organic phases are washed with saturated sodium chloride solution and dried with sodium sulfate, and then the solvent is removed in a rotary evaporator. The residue is purified by column chromatography (silica gel, mobile phase: cyclohexane/ethyl acetate 10:1). 3.32 g (78% of theory) of the title compound are obtained with a purity of 80% (according to LC-MS).

MS (EIpos): m/z=215 [M]$^+$ $^1$H-NMR (300 MHz, DMSO-d$_6$): δ=7.85-7.91 (m, 3H), 10.20 (s, 1H).

Example 8A

4-Cyano-2-methoxyphenyl trifluoromethanesulfonate

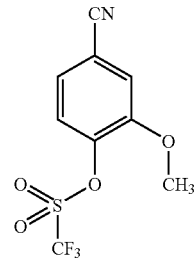 [SMILES: COc1cc(C#N)ccc1OS(=O)(=O)C(F)(F)F]

24 ml (141 mmol) of trifluoromethanesulfonic anhydride are slowly added dropwise to a solution of 20 g (134 mmol) of 4-hydroxy-3-methoxybenzonitrile in pyridine (80 ml), keeping the reaction temperature below 25° C. with the aid of an ice bath. The suspension is then stirred at RT for 1 h. Ice-water (400 ml) is added, and the suspension is stirred further until room temperature is reached. It is then filtered, the solid is dissolved in ethyl acetate, and the solution is washed with saturated sodium chloride solution. The organic phase is dried over magnesium sulfate and concentrated. 37.13 g (92% of theory) of the title compound are obtained as a white solid.

LC-MS (method 3): $R_t$=2.54 min; MS (EIpos): m/z=282 [M+H]$^+$ $^1$H-NMR (300 MHz, DMSO-d$_6$): δ=3.97 (s, 3H), 7.60 (dd, 1H), 7.71 (d, 1H), 7.92 (d, 1H).

Example 9A tert-Butyl (2E)-3-(4-cyano-2-methoxyphenyl)acrylate

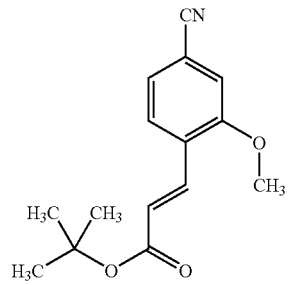 [SMILES: COc1cc(C#N)ccc1/C=C/C(=O)OC(C)(C)C]

4 g (5.7 mmol) of bis(triphenylphosphine)palladium(II) chloride are added to a degassed solution of 37.13 g (132 mmol) of 4-cyano-2-methoxyphenyl trifluoromethanesulfonate, 35 ml (245 mmol) of tert-butyl acrylate and 90 ml (645 mmol) of triethylamine in DMF (250 ml). The solution is stirred at 100° C. under a protective gas atmosphere for 24 h. Ice-water (1000 ml) is then added, and the suspension is extracted with ethyl acetate (3×100 ml). The organic phase is washed with saturated sodium chloride solution, dried over magnesium sulfate and concentrated. The residue is purified by column chromatography (silica gel, mobile phase: cyclohexane/ethyl acetate 10:1). 24.6 g (72% of theory) of the title compound are obtained as a white solid.

LC-MS (method 1): $R_t$=2.59 min; MS (Elpos): m/z=260 $[M+H]^+$ $^1$H-NMR (300 MHz, DMSO-$d_6$): δ=1.48 (s, 9H), 3.93 (s, 3H), 6.65 (d, 1H), 7.42 (d, 1H), 7.58 (s, 1H), 7.74 (d, 1H), 7.89 (d, 1H).

Example 10A

4-Formyl-3-methoxybenzonitrile

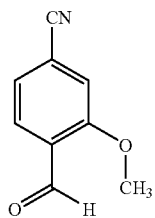

79 g (370 mmol) of sodium metaperiodate are added in portions to a vigorously stirred solution of 48 g (185 mmol) of tert-butyl (2E)-3-(4-cyano-2-methoxyphenyl)acrylate, 207 mg (0.81 mmol) of osmium tetroxide and 1.4 g (6.14 mmol) of benzyltriethylammonium chloride in 750 ml of water/THF (2:1), keeping the reaction temperature below 30° C. The solution is stirred at RT for a further 1 h. Water (2000 ml) is added and the mixture is then filtered. The remaining solid is dissolved in ethyl acetate, and the solution is washed with saturated sodium chloride solution. The organic phase is dried over magnesium sulfate and concentrated. The residue is stirred with petroleum ether. 21.18 g (71% of theory) of the title compound are obtained as a white solid.

LC-MS (method 3): $R_t$=1.87 min; MS (Elpos): m/z=162 $[M+H]^+$ $^1$H-NMR (300 MHz, DMSO-$d_6$): δ=3.98 (s, 3H), 7.53 (d, 1H), 7.80 (s, 1H), 7.81 (d, 1H), 10.37 (s, 1H).

Example 11A

4-Formyl-3-hydroxybenzonitrile

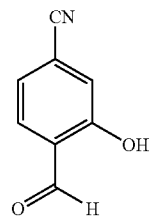 [SMILES: N#Cc1ccc(C=O)c(O)c1]

100 ml of a boron tribromide solution in dichloromethane (1 M, 100 mmol) are added dropwise to a solution of 8 g (49.64 mmol) of 4-formyl-3-methoxybenzonitrile in 80 ml of anhydrous dichloromethane at −78° C. under an argon atmosphere. The reaction mixture is stirred at RT until the precursor has completely reacted (about 5 days). The reaction solution is then neutralized at 0° C. with saturated sodium bicarbonate solution. The phases are separated and the organic phase is washed with saturated sodium chloride solution, dried over magnesium sulfate and concentrated. The residue is purified by column chromatography on silica gel (mobile phase: cyclohexane/ethyl acetate 3:1). 4.5 g (61% of theory) of the title compound are obtained as a yellow solid.

LC-MS (method 1): $R_t$=1.38 min; $[M-H]^-$=146

$^1$H-NMR (300 MHz, CDCl$_3$): δ=7.38 (d, 1H), 7.38 (s, 1H), 7.77 (d, 1H), 10.33 (s, 1H), 11.38 (s, 1H).

Example 12A

5-Cyano-2-formylphenyl trifluoromethanesulfonate

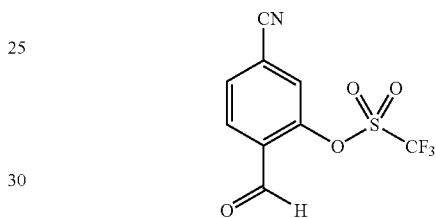

2.4 ml (14.27 mmol) of trifluoromethanesulfonic anhydride are added dropwise to a solution of 2 g (13.59 mmol) of 4-formyl-3-hydroxybenzonitrile and 2.5 ml (14.27 mmol) of N,N-diisopropyl-ethylamine in 37 ml of anhydrous dichloromethane at 0° C. under an argon atmosphere. The reaction mixture is stirred at RT for 1 h, then diluted with 70 ml of dichloromethane and washed successively with 1 M hydrochloric acid, saturated sodium bicarbonate solution and saturated sodium chloride solution. The organic solution is dried over magnesium sulfate and concentrated. The residue is purified by column chromatography on silica gel (mobile phase: cyclohexane/ethyl acetate 7:1). 2.36 g (62% of theory) of the title compound are obtained as a white solid.

LC-MS (method 3): $R_t$=2.34 min; $[M+H]^+$=280

$^1$H-NMR (300 MHz, CDCl$_3$): δ=8.27 (m, 2H), 8.33 (s, 1H), 10.13 (s, 1H).

Example 13A

4-Formyl-3-vinylbenzonitrile

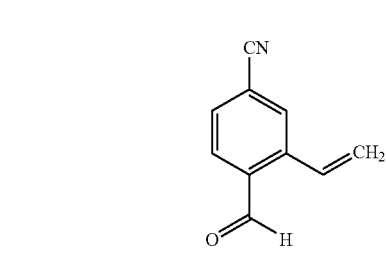

125 mg (0.18 mmol) of bis(triphenylphosphine)palladium (II) chloride are added to a solution of 1 g (3.58 mmol) of 5-cyano-2-formylphenyl trifluoromethanesulfonate and 1.15 ml (3.94 mmol) of tri-n-butylvinylstannane in 6 ml of anhydrous and degassed DMF under an argon atmosphere. The reaction mixture is then stirred at 80° C. for 90 min. Subsequently, 100 ml of 10% strength potassium fluoride solution are added, and the mixture is stirred at RT for 1 h. The suspension is extracted three times with 20 ml of ethyl acetate each time, and the combined organic phases are washed successively with saturated sodium bicarbonate solution and saturated sodium chloride solution. The organic solution is dried over magnesium sulfate and concentrated. The residue (0.6 g) is employed without further purification in the next stage.

GC-MS (method 5): $R_t$=5.02 min; $[M]^+$=157

$^1$H-NMR (300 MHz, CDCl$_3$): δ=5.62 (d, 1H), 6.05 (d, 1H), 7.58 (dd, 1H), 7.95 (d, 1H), 8.00 (d, 1H), 8.24 (s, 1H), 10.32 (s, 1H).

Example 14A

3-Ethyl-4-formylbenzonitrile

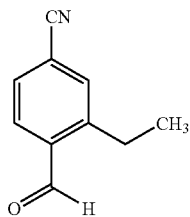

A solution of 1.3 g (8.27 mmol) of 4-formyl-3-vinylbenzonitrile in 35 ml of ethanol is mixed with 880 mg of 10% palladium on carbon and vigorously stirred under a hydrogen atmosphere for 2 h. The suspension is filtered through a layer of kieselguhr, the residue is washed with ethanol, and the filtrate is concentrated. The residue (890 mg) is employed without further purification in the following stage.

$^1$H-NMR (300 MHz, CDCl$_3$): δ=1.2 (t, 1H), 3.07 (q, 2H), 7.88 (d, 1H), 7.90 (s, 1H), 7.97 (d, 1H), 10.32 (s, 1H).

Example 15A

Methyl 4-cyano-2-fluorobenzoate

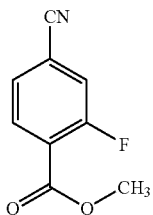

13.20 g (79.9 mmol) of 4-cyano-2-fluorobenzoic acid are dissolved in 300 ml of acetone. Then 22.10 g (159.9 mmol) of potassium carbonate and 9.08 ml (95.9 mmol) of dimethyl sulfate are successively added. The mixture is stirred at reflux temperature for 20 h. The reaction mixture is then mixed with 300 ml of water and the acetone is removed in a rotary evaporator. Several extractions with dichloromethane are carried out. The combined organic phases are washed with saturated sodium chloride solution and dried over sodium sulfate. The solvent is then removed in vacuo. The remaining solid is used further without further purification. 16.1 g (84% of theory) of the title compound are obtained as a colorless solid.

GC-MS (method 5): $R_t$=6.23 min; $[M]^+$ (EIpos): m/z=179

$^1$H-NMR (300 MHz, DMSO-d$_6$): δ=3.90 (s, 3H), 7.83 (dd, 1H), 8.01-8.08 (m, 2H).

Example 16A

3-Fluoro-4-(hydroxymethyl)benzonitrile

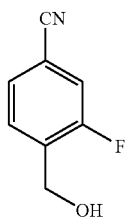 [SMILES: N#Cc1ccc(CO)c(F)c1]

16.10 g (89.9 mmol) of methyl 4-cyano-2-fluorobenzoate are dissolved in 150 ml of methanol. Then 3.40 g (89.9 mmol) of sodium borohydride are added in portions. After the reaction has taken place (TLC check), the mixture is adjusted to pH 3 with dilute hydrochloric acid and extracted several times with dichloromethane. The combined organic phases are washed with saturated sodium chloride solution and dried with magnesium sulfate. The solvent is then removed in vacuo, and the residue is purified by column chromatography (silica gel, mobile phase: cyclohexane/ethyl acetate 15:1→3:7). 3.70 g (27.2% of theory) of the title compound are obtained.

GC-MS (method 5): $R_t$=6.51 min; $[M]^+$ (EIpos): m/z=151

$^1$H-NMR (300 MHz, DMSO-d$_6$): δ=4.61 (s, 2H), 5.53 (s, 1H), 7.61-7.74 (m, 2H), 7.79 (dd, 1H).

Example 17A

3-Fluoro-4-formylbenzonitrile

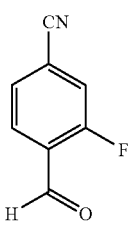

1.00 g (6.62 mmol) of 3-fluoro-4-(hydroxymethyl)benzonitrile are dissolved in 50 ml of dichloromethane, and 9.20 g (105.9 mmol) of manganese(IV) oxide are added. The mixture is stirred at room temperature overnight and then filtered through a short kieselguhr column. The solvent is distilled out under reduced pressure, and the residue is purified by column chromatography (silica gel, mobile phase: dichloromethane). 120 mg (12.1% of theory) of the title compound are obtained.

GC-MS (method 5): $R_t$=5.11 min; $[M]^+$ (EIpos): m/z=149

$^1$H-NMR (300 MHz, DMSO-d$_6$): δ=7.89 (d, 1H), 8.00 (t, 1H), 8.11 (d, 1H), 10.24 (d, 1H).

Example 18A

3-Chloro-4-formylbenzonitrile

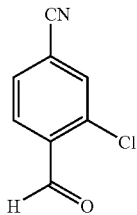 [SMILES: N#Cc1ccc(C=O)c(Cl)c1]

25.0 g (164.91 mmol) of 3-chloro-4-methylbenzonitrile are dissolved in 150 ml of DMF, and 25.55 g (214.39 mmol) of N,N-dimethylformamide dimethyl acetal are added. The mixture is stirred in an oil bath at a temperature of 140° C. for 20 h and then at 180° C. for 4 h. The volatile components are removed in a rotary evaporator, and the remaining residue is directly reacted further.

The crude 3-chloro-4-[2-(dimethylamino)vinyl]benzonitrile obtained in this way is taken up in 500 ml of THF/water (1:1), and 77.6 g (362.9 mmol) of sodium periodate are added. The mixture is stirred at room temperature for 18 h, and then the precipitate which has separated out is removed by filtration. The filtrate is mixed with saturated sodium bicarbonate solution and extracted three times with ethyl acetate. The combined organic phases are dried with sodium sulfate, and the solvent is removed in a rotary evaporator. The crude product is purified by column chromatography (silica gel, mobile phase: cyclohexane/ethyl acetate 7:3). 3.0 g (15% of theory) of the title compound are obtained.

GC-MS (method 5): R$_t$=6.64 min; [M]$^+$ (Elpos): m/z=165
$^1$H-NMR (300 MHz, DMSO-d$_6$): δ=7.97-8.03 (m, 2H), 8.27 (s, 1H), 10.34 (d, 1H).

Example 19A

4-Formyl-1-naphthonitrile

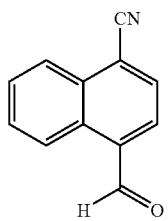 [SMILES: N#Cc1ccc(C=O)c2ccccc12]

2.50 g (14.95 mmol) of 4-methyl-1-naphthonitrile are dissolved in 40 ml of tetrachloromethane and 3.19 g (17.94 mmol) of N-bromosuccinimide and 245 mg (1.50 mmol) of 2,2'-azobis-2-methyl-propanenitrile are added. The mixture is stirred at the reflux temperature overnight. After cooling, the product is filtered off 2.75 g (74.7% of theory) of 4-(bromomethyl)-1-naphthonitrile are obtained in a purity of 90% and are reacted without further purification.

2.75 g (11.17 mmol) of the bromide obtained in this way are dissolved in 60 ml of acetonitrile, and 2 g of molecular sieves (3 Å) are added. Then 1.44 g (12.29 mmol) of N-methylmorpholine N-oxide are added, and the mixture is stirred at room temperature overnight. The mixture is then filtered through silica gel and the filtrate is concentrated. The residue is purified on a Biotage cartridge (40 M) (eluent: isohexane/ethyl acetate 3:1). The product fractions are combined, the solvent is removed in a rotary evaporator, and the residue is then stirred with diethyl ether, whereupon crystallization occurs. The product is washed with a little diethyl ether and dried under high vacuum. 254 mg (12.6% of theory) of the title compound are obtained.

LC-MS (method 3): R$_t$=2.27 min; [M+H]$^+$(Elpos): m/z=182
$^1$H-NMR (300 MHz, CDCl$_3$): δ=7.79-7.87 (m, 2H), 8.05 (d, 1H), 8.09 (d, 1H), 8.37 (m, 1H), 9.27 (m, 1H), 10.51 (s, 1H).

Example 20A

2-Cyanoethyl 4-(4-cyano-2-methoxyphenyl)-2-methyl-5-oxo-1,4,5,6-tetrahydro-1,6-naphthyridine-3-carboxylate

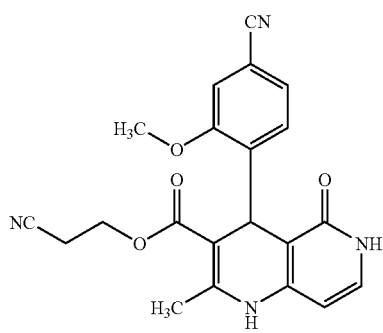

14.63 g (90.81 mmol) of the compound from Example 10A, 10.00 g (90.81 mmol) of 4-aminopyridin-2(1H)-one [Searls, T., McLaughlin, L. W., *Tetrahedron* 55, 11985-11996 (1999)] and 15.65 g (90.81 mmol) of 2-cyanoethyl 3-oxobutanoate [Yamamoto, T., et al., *Bioorg. Med. Chem. Lett.* 16, 798-802 (2006)] are dissolved in 300 ml of isopropanol and stirred at the reflux temperature under argon for 3 days. The mixture is then concentrated and subsequently purified by column chromatography (silica gel; mobile phase: initially ethyl acetate and then dichloromethane/methanol 10:1). The resulting product fractions are concentrated and then taken up in a little ethyl acetate. The precipitated product is filtered off and dried at 40° C. in vacuo overnight. 10.11 g (27% of theory) of the title compound are obtained.

LC-MS (method 6): R$_t$=1.83 min; MS (Elpos): m/z=391 [M+H]$^+$

¹H-NMR (300 MHz, DMSO-d₆): δ=2.27 (s, 3H), 2.79 (m, 2H), 3.75 (s, 3H), 3.96-4.14 (m, 2H), 5.19 (s, 1H), 5.87 (d, 1H), 7.10 (d, 1H), 7.23 (dd, 1H), 7.30-7.35 (m, 2H), 9.30 (s, 1H), 10.83 (s, 1H).

Example 21A

2-Cyanoethyl 4-(4-cyano-2-methoxyphenyl)-5-ethoxy-2-methyl-1,4-dihydro-1,6-naphthyridine-3-carboxylate

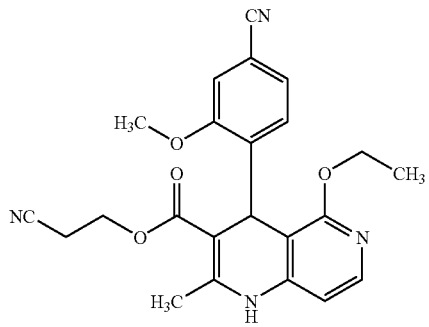

10.00 g (25.62 mmol) of the compound from Example 20A are suspended in 250 ml of triethyl orthoformate and heated to 130° C. Then, over a total period of 8 hours, 15 drops of concentrated sulfuric acid are added each hour to the reaction mixture. It is then stirred at the same temperature overnight. After cooling, excess orthoester is removed in a rotary evaporator, and the crude product is purified by column chromatography (silica gel; mobile phase: cyclohexane/ethyl acetate 1:1). 7.20 g (65% of theory) of the title compound are obtained.

LC-MS (method 6): $R_t$=2.82 min; MS (Elpos): m/z=419 [M+H]⁺

¹H-NMR (300 MHz, DMSO-d₆): δ=1.12 (t, 3H), 2.33 (s, 3H), 2.77 (m, 2H), 3.78 (s, 3H), 3.99-4.13 (m, 4H), 5.37 (s, 1H), 6.48 (d, 1H), 7.25 (dd, 1H), 7.29-7.35 (m, 2H), 7.73 (d, 1H), 9.53 (s, 1H).

Example 22A 4-(4-Cyano-2-methoxyphenyl)-5-ethoxy-2-methyl-1,4-dihydro-1,6-naphthyridine-3-carboxylic acid

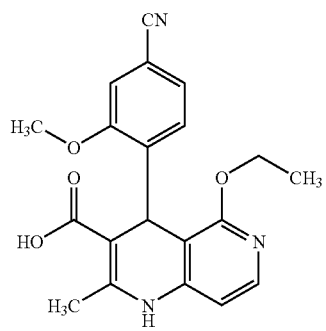 [SMILES: CCOc1nccc2c1C(c1ccc(C#N)cc1OC)C(C(=O)O)=C(C)N2]

7.20 g (17.21 mmol) of the compound from Example 21A are dissolved in 200 ml of 1,2-dimethoxyethane/water (3:1 v/v), mixed with 34.42 ml (34.42 mmol) of 1 N sodium hydroxide solution and stirred at room temperature overnight. The mixture is then mixed with 100 ml of diethyl ether and 100 ml of water, the organic phase is separated off, and the aqueous phase is adjusted to pH 4-5 with 1N hydrochloric acid. The resulting suspension is stirred for 1 h and the precipitated solid is then removed by filtration. The precipitate is washed with water and a little diethyl ether. Drying in vacuo at 40° C. results in 3.57 g (57% of theory) of the title compound.

LC-MS (method 7): $R_t$=2.32 min; MS (Elpos): m/z=366 [M+H]⁺

¹H-NMR (300 MHz, DMSO-d₆): δ=1.12 (t, 3H), 2.28 (s, 3H), 3.74 (s, 3H), 4.07 (m, 2H), 5.33 (s, 1H), 6.44 (d, 1H), 7.23-7.29 (m, 2H), 7.32 (s, 1H), 7.70 (d, 1H), 9.25 (s, 1H), 11.34 (s, 1H).

Example 23A

4-[5-Ethoxy-3-(1H-imidazol-1-ylcarbonyl)-2-methyl-1,4-dihydro-1,6-naphthyridin-4-yl]-3-methoxybenzonitrile

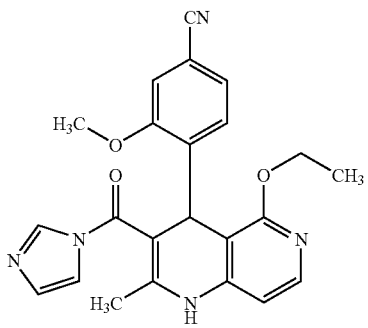 [SMILES: CCOc1nccc2c1C(c1ccc(C#N)cc1OC)C(C(=O)n1ccnc1)=C(C)N2]

1.20 g (3.28 mmol) of the compound from Example 22A are introduced into 25 ml of ethyl acetate and, after addition of 0.666 g (4.11 mmol) of 1,1'-carbonyldiimidazole, stirred at room temperature overnight. The reaction mixture is concentrated in a rotary evaporator, and the crude product obtained in this way is employed without purification for further reactions.

MS (Elpos): m/z=416 [M+H]⁺.

Example 24A

2-Cyanoethyl 2-(4-cyano-2-methoxybenzylidene)-3-oxobutanoate

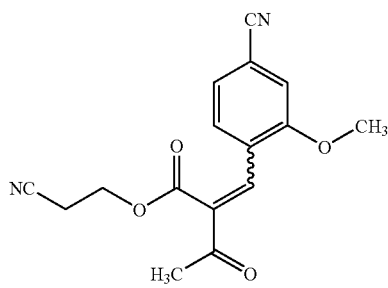

3.00 g (18.62 mmol) of the compound from Example 10A, 3.18 g (20.48 mmol) of 2-cyanoethyl 3-oxobutanoate [Yamamoto, T., et al., *Bioorg. Med. Chem. Lett.* 16, 798-802 (2006)], 213 µl (3.72 mmol) of acetic acid and 368 µl (3.72 mmol) of piperidine are dissolved in 50 ml of anhydrous dichloromethane and stirred under reflux with a water trap overnight. The volatile components are then removed in a rotary evaporator, and the residue is purified by column chromatography (silica gel; mobile phase: gradient cyclohexane/ethyl acetate 7:3→1:1). 2.77 g (48% of theory) of the title compound are obtained as a mixture of the E/Z isomers.

LC-MS (method 7): $R_t$=2.89 and 3.00 min; MS (Elpos): m/z=299 [M+H]$^+$.

Example 25A

2-Cyanoethyl 4-(4-cyano-2-methoxyphenyl)-2,7-dimethyl-5-oxo-1,4,5,6-tetrahydro-1,6-naphthyridine-3-carboxylate

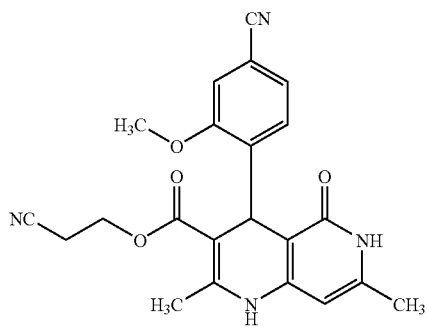

1.49 g (5.00 mmol) of the compound from Example 24A are introduced into 30 ml of 2-propanol, mixed with 620 mg (5.00 mmol) of 4-amino-6-methylpyridin-2(1H)-one [Bisagni, E., Hung, N. C., *Synthesis*, 765-766 (1984)] and then stirred at the reflux temperature overnight. After cooling, the precipitate is filtered off, washed with diethyl ether and dried under high vacuum. 1.53 g (76% of theory) of the title compound are obtained.

LC-MS (method 3): $R_t$=1.73 min; MS (Elpos): m/z=405 [M+H]$^+$ $^1$H-NMR (300 MHz, DMSO-d$_6$): δ=2.05 (s, 3H), 2.26 (s, 3H), 2.78 (m, 2H), 3.74 (s, 3H), 3.96-4.13 (m, 2H), 5.14 (s, 1H), 5.64 (d, 1H), 7.23 (dd, 1H), 7.28-7.33 (m, 2H), 9.22 (s, 1H), 10.82 (s, 1H).

Example 26A

2-Cyanoethyl 4-(4-cyano-2-methoxyphenyl)-5-ethoxy-2,7-dimethyl-1,4-dihydro-1,6-naphthyridine-3-carboxylate

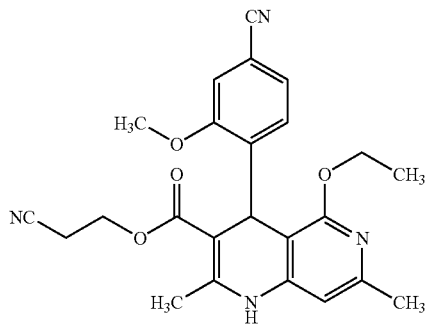

1.52 g (3.76 mmol) of the compound from Example 25A are suspended in 40 ml of triethyl orthoformate and heated to 130° C. Then, over a total period of 8 hours, 10 drops of concentrated sulfuric acid are added each hour to the reaction mixture. It is then stirred at the same temperature overnight. After cooling, excess orthoester is removed in a rotary evaporator, and the crude product is purified by column chromatography (silica gel; mobile phase: cyclohexane/ethyl acetate 1:1). The product fractions are combined, the solvent is removed, and the residue is taken up in a little methanol. The crystallizing product is filtered off. Drying under high vacuum results in 1.09 g (67% of theory) of the title compound.

LC-MS (method 3): $R_t$=2.23 min; MS (Elpos): m/z=433 [M+H]$^+$ $^1$H-NMR (300 MHz, DMSO-d$_6$): δ=1.11 (t, 3H), 2.20 (s, 3H), 2.32 (s, 3H), 2.76 (m, 2H), 3.78 (s, 3H), 3.97-4.12 (m, 4H), 5.32 (s, 1H), 6.30 (s, 1H), 7.24 (d, 1H), 7.27-7.32 (m, 2H), 9.43 (s, 1H).

Example 27A 4-(4-Cyano-2-methoxyphenyl)-5-ethoxy-2,7-dimethyl-1,4-dihydro-1,6-naphthyridine-3-carboxylic acid

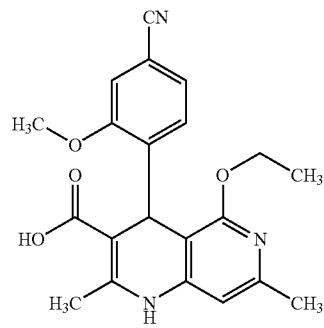 [SMILES: CCOc1nc(C)cc2c1C(c1ccc(C#N)cc1OC)C(C(=O)O)=C(C)N2]

642 mg (2.52 mmol) of the compound from Example 26A are dissolved in 40 ml of 1,2-dimethoxyethane/water (3:1 v/v), mixed with 5.04 ml (5.04 mmol) of 1 N sodium hydroxide solution and stirred at room temperature overnight. The mixture is then mixed with 30 ml of diethyl ether and 30 ml of water, the organic phase is separated off, and the aqueous phase is adjusted to pH 4-5 with 1 N hydrochloric acid. The resulting suspension is stirred for 1 h, and the precipitated solid is then removed by filtration. The precipitate is washed with water and a little diethyl ether. Drying at 40° C. in vacuo results in 642 mg (67% of theory) of the title compound.

LC-MS (method 3): $R_t$=1.87 min; MS (Elpos): m/z=380 [M+H]$^+$

¹H-NMR (300 MHz, DMSO-d₆): δ=1.11 (t, 3H), 2.19 (s, 3H), 2.28 (s, 3H), 3.74 (s, 3H), 4.05 (m, 2H), 5.28 (s, 1H), 6.27 (s, 1H), 7.20-7.28 (m, 2H), 7.31 (s, 1H), 9.17 (s, 1H), 11.31 (s, 1H).

Example 28A

2-Cyanoethyl 4-(4-cyano-2-methoxyphenyl)-2,8-dimethyl-5-oxo-1,4,5,6-tetrahydro-1,6-naphthyridine-3-carboxylate

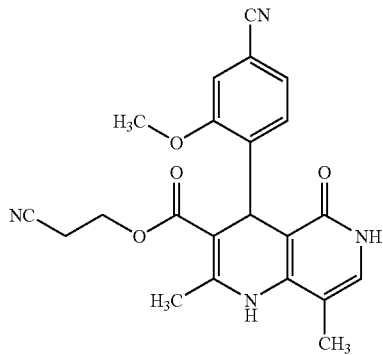

2.69 g (9.00 mmol) of the compound from Example 24A are introduced into 45 ml of 2-propanol, mixed with 1.17 g (9.00 mmol) of 4-amino-5-methylpyridin-2(1H)-one [Bisagni, E., Hung, N. C., *Synthesis*, 765-766 (1984)] and then stirred at the reflux temperature overnight. After cooling, the precipitate is filtered off, washed with diethyl ether and dried under high vacuum. 2.22 g (61% of theory) of the title compound are obtained.

LC-MS (method 3): $R_t$=1.75 min; MS (EIpos): m/z=405 [M+H]⁺

¹H-NMR (300 MHz, DMSO-d₆): δ=2.03 (s, 3H), 2.35 (s, 3H), 2.80 (m, 2H), 3.74 (s, 3H), 4.04 (m, 1H), 4.11 (m, 1H), 5.20 (s, 1H), 6.95 (s, 1H), 7.23 (dd, 1H), 7.28-7.33 (m, 2H), 8.18 (s, 1H), 10.76 (s, 1H).

Example 29A

2-Cyanoethyl 4-(4-cyano-2-methoxyphenyl)-5-ethoxy-2,8-dimethyl-1,4-dihydro-1,6-naphthyridine-3-carboxylate

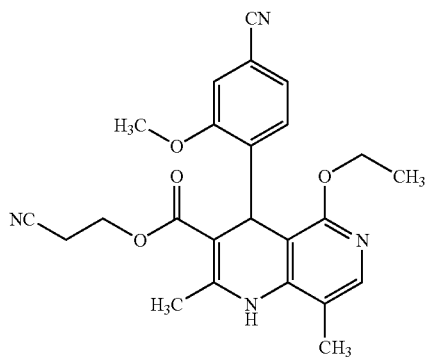

2.22 g (5.44 mmol) of the compound from Example 28A are suspended in 100 ml of triethyl orthoformate and heated to 130° C. Then, over a total period of 8 hours, 10 drops of concentrated sulfuric acid are added each hour to the reaction mixture. It is then stirred at the same temperature overnight. After cooling, excess orthoester is removed in a rotary evaporator, and the crude product is purified by column chromatography (silica gel; mobile phase: initially dichloromethane then isohexane/ethyl acetate 1:1). The product fractions are combined, the solvent is removed, and the residue is crystallized from ethyl acetate/diethyl ether. The precipitate is filtered off and dried under high vacuum. 1.80 g (77% of theory) of the title compound are obtained.

LC-MS (method 6): $R_t$=3.02 min; MS (EIpos): m/z=433 [M+H]⁺

¹H-NMR (300 MHz, DMSO-d₆): δ=1.11 (t, 3H), 2.16 (s, 3H), 2.42 (s, 3H), 2.78 (m, 2H), 3.77 (s, 3H), 4.01-4.13 (m, 4H), 5.37 (s, 1H), 7.25 (d, 1H), 7.28-7.33 (m, 2H), 7.60 (s, 1H), 8.35 (s, 1H).

Example 30A 4-(4-Cyano-2-methoxyphenyl)-5-ethoxy-2,8-dimethyl-1,4-dihydro-1,6-naphthyridine-3-carboxylic acid

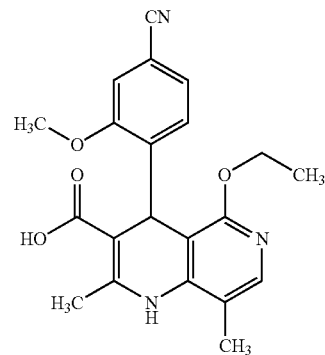 [SMILES: CCOc1ncc(C)c2c1C(c1ccc(C#N)cc1OC)C(C(=O)O)=C(C)N2]

1.75 g (4.05 mmol) of the compound from Example 29A are dissolved in 60 ml of 1,2-dimethoxyethane/water (2:1 v/v), 8.09 ml (8.09 mmol) of 1 N sodium hydroxide solution are added, and the mixture is stirred at room temperature for one hour. 30 ml of diethyl ether are then added to the mixture, and the aqueous phase is acidified with 6 N hydrochloric acid. The resulting precipitate is filtered off and washed with water and a little diethyl ether. Drying in a vacuum drying oven at 40° C. results in 1.47 g (96% of theory) of the title compound.

LC-MS (method 7): $R_t$=2.50 min; MS (EIpos): m/z=380 [M+H]⁺

¹H-NMR (300 MHz, DMSO-d₆): δ=1.14 (t, 3H), 2.14 (s, 3H), 2.37 (s, 3H), 3.73 (s, 3H), 4.04 (m, 2H), 5.33 (s, 1H), 7.26 (m, 2H), 7.32 (s, 1H), 7.57 (s, 1H), 8.16 (s, 1H), 11.43 (br. s, 1H).

Example 31A

2-Cyanoethyl 2-methyl-4-(2-methyl-4-oxo-4H-chromen-8-yl)-5-oxo-1,4,5,6-tetrahydro-1,6-naphthyridine-3-carboxylate

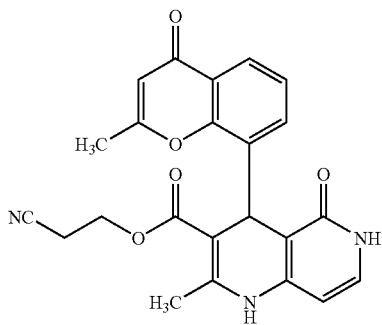

3.00 g (15.94 mmol) of the compound from Example 5A, 1.75 g (15.94 mmol) of 4-aminopyridin-2(1H)-one [Searls, T., McLaughlin, L. W., *Tetrahedron* 55, 11985-11996 (1999)] and 2.47 g (15.94 mmol) of 2-cyanoethyl 3-oxobutanoate [Yamamoto, T., et al., *Bioorg. Med. Chem. Lett.* 16, 798-802 (2006)] are dissolved in 60 ml of ethanol and stirred at the reflux temperature under argon overnight. The precipitated product is then filtered off, washed with ethanol and diethyl ether and dried under high vacuum. 2.30 g (35% of theory) of the title compound are obtained in the form of beige-colored crystals.

LC-MS (method 7): $R_t$=1.59 min; MS (Elpos): m/z=418 [M+H]$^+$.

Example 32A

2-Cyanoethyl 5-ethoxy-2-methyl-4-(2-methyl-4-oxo-4H-chromen-8-yl)-1,4-dihydro-1,6-naphthyridine-3-carboxylate

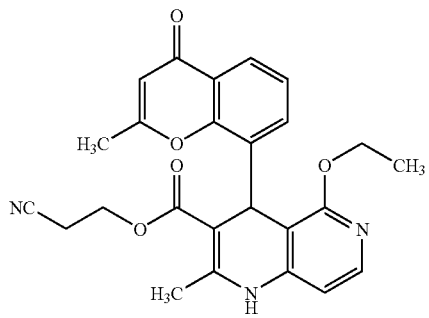

2.20 g (5.27 mmol) of the compound from Example 31A are suspended in 80 ml of triethyl orthoformate and heated to 130° C. Then, over a total period of 8 hours, 5 drops of concentrated sulfuric acid are added each hour to the reaction mixture. It is then stirred at the same temperature overnight. After cooling, excess orthoester is removed in a rotary evaporator, and the crude product is purified by column chromatography (silica gel; mobile phase: initially dichloromethane, then ethyl acetate, finally ethyl acetate/methanol 20:1). The product fractions are concentrated to a volume of about 5 ml. The precipitated product is filtered off and, after washing with ethyl acetate and diethyl ether, dried under high vacuum. 282 mg (12% of theory) of the title compound are obtained in the form of brown crystals.

LC-MS (method 3): $R_t$=1.96 min; MS (Elpos): m/z=446 [M+H]$^+$ $^1$H-NMR (300 MHz, DMSO-d$_6$): δ=1.01 (t, 3H), 2.38 (s, 6H), 2.74 (m, 2H), 3.96-4.13 (m, 4H), 5.54 (s, 1H), 6.19 (s, 1H), 6.53 (d, 1H), 7.31 (t, 1H), 7.67 (dd, 1H), 7.76 (d, 1H), 7.80 (dd, 1H), 9.69 (s, 1H).

Example 33A

5-Ethoxy-2-methyl-4-(2-methyl-4-oxo-4H-chromen-8-yl)-1,4-dihydro-1,6-naphthyridine-3-carboxylic acid

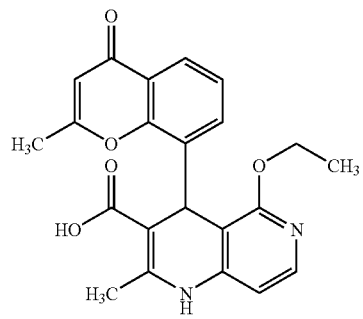 [SMILES: CCOc1nccc2c1C(c1cccc3c(=O)cc(C)oc13)C(C(=O)O)=C(C)N2]

270 mg (0.61 mmol) of the compound from Example 32A are dissolved in 15 ml of 1,2-dimethoxyethane/water (2:1 v/v), 1.21 ml (1.21 mmol) of 1 N sodium hydroxide solution are added, and the mixture is stirred at room temperature for 1 h. 30 ml of diethyl ether are then added to the reaction mixture. The aqueous phase is separated off and acidified with 1 N hydrochloric acid. The resulting precipitate is filtered off and washed with water and a little diethyl ether. Drying in vacuo at 40° C. results in 167 mg (70% of theory) of the title compound.

LC-MS (method 7): $R_t$=2.01 min; MS (Elpos): m/z=393 [M+H]$^+$ $^1$H-NMR (300 MHz, DMSO-d$_6$): δ=1.02 (t, 3H), 2.33 (s, 3H), 2.35 (s, 3H), 3.97 (m, 1H), 4.08 (m, 1H), 5.52 (s, 1H), 6.18 (s, 1H), 6.50 (d, 1H), 7.31 (t, 1H), 7.60 (dd, 1H), 7.74 (d, 1H), 7.79 (dd, 1H), 9.42 (s, 1H), 11.45 (br. s, 1H).

Example 34A

2-Cyanoethyl 4-[4-bromo-2-(trifluoromethoxy)phenyl]-2-methyl-5-oxo-1,4,5,6-tetrahydro-1,6-naphthyridine-3-carboxylate

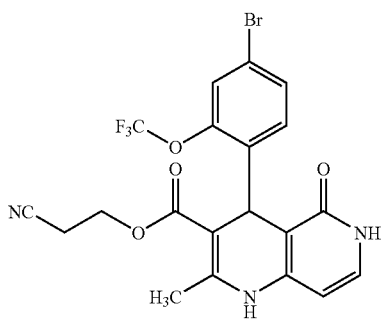

10.00 g (31.17 mmol) of the compound from Example 6A and 6.41 g (31.17 mmol) of 2-cyanoethyl 3-oxobutanoate [Yamamoto, T., et al., *Bioorg. Med. Chem. Lett.* 16, 798-802 (2006)] are introduced into 100 ml of 2-propanol and, after adding 4.09 g (37.17 mmol) of 4-aminopyridin-2(1H)-one [Searls, T., McLaughlin, L. W., *Tetrahedron* 55, 11985-11996 (1999)], stirred at the reflux temperature for three days. After cooling, the solvent is removed under reduced pressure, and the crude product is purified by column chromatography (silica gel; mobile phase: dichloromethane/methanol 10:1). 7.38 g (36% of theory) of the title compound are obtained.

LC-MS (method 6): $R_t$=2.84 min; MS (EIpos): m/z=499 [M+H]$^+$.

Example 35A

2-Cyanoethyl 4-[4-bromo-2-(trifluoromethoxy)phenyl]-5-ethoxy-2-methyl-1,4-dihydro-1,6-naphthyridine-3-carboxylate

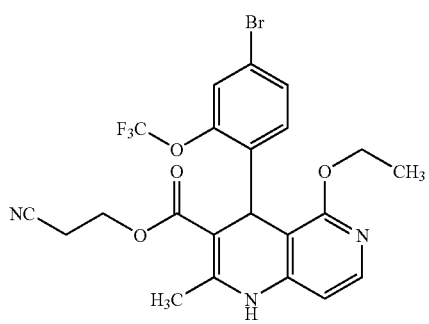

7.30 g (13.19 mmol) of the compound from Example 34A are suspended in 150 ml of triethyl orthoformate and heated to 130° C. Then, over a total period of 7 hours, 15 drops of concentrated sulfuric acid are added each hour to the reaction mixture. It is then stirred at the same temperature overnight. After cooling, excess orthoester is removed in a rotary evaporator, and the crude product is purified by column chromatography (silica gel; mobile phase: cyclohexane/ethyl acetate 1:1). 4.59 g (64% of theory) of the title compound are obtained.

LC-MS (method 3): $R_t$=2.74 min; MS (EIpos): m/z=527 [M+H]$^+$ $^1$H-NMR (300 MHz, DMSO-d$_6$): δ=1.17 (t, 3H), 2.33 (s, 3H), 2.81 (m, 2H), 3.99-4.21 (m, 4H), 5.29 (s, 1H), 6.50 (d, 1H), 7.31 (t, 1H), 7.37 (d, 1H), 7.44 (dd, 1H), 7.78 (d, 1H), 9.63 (s, 1H).

Example 36A

2-Cyanoethyl 4-[4-cyano-2-(trifluoromethoxy)phenyl]-5-ethoxy-2-methyl-1,4-dihydro-1,6-naphthyridine-3-carboxylate

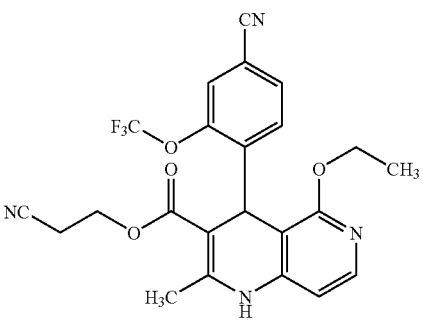

4.59 g (8.72 mmol) of the compound from Example 35A, 758 mg (6.45 mmol) of zinc cyanide and 504 mg (0.436 mmol) of tetrakis(triphenylphosphine)palladium(0) are dissolved in 40 ml of DMF and then, divided into three mixtures, heated in a single mode microwave (Emrys Opzimizer) at 220° C. for 5 min. The individual mixtures are then recombined, and the solvent is removed in a rotary evaporator. The crude product is taken up in ethyl acetate and filtered through kieselguhr. The organic phase is washed with water (2×) and with saturated sodium chloride solution. After removal of the solvent by distillation, the crude product is purified by column chromatography (silica gel; mobile phase: cyclohexane/ethyl acetate 7:3→1:1). 1.40 g (31% of theory) of the title compound are obtained.

LC-MS (method 3): $R_t$=2.48 min; MS (EIpos): m/z=473 [M+H]$^+$ $^1$H-NMR (300 MHz, DMSO-d$_6$): δ=1.10 (t, 3H), 2.34 (s, 3H), 2.80 (m, 2H), 4.00-4.21 (m, 4H), 5.36 (s, 1H), 6.51 (d, 1H), 7.60 (d, 1H), 7.66-7.74 (2H), 7.79 (d, 1H), 9.70 (s, 1H).

Example 37A

4-[4-Cyano-2-(trifluoromethoxy)phenyl]-5-ethoxy-2-methyl-1,4-dihydro-1,6-naphthyridine-3-carboxylic acid

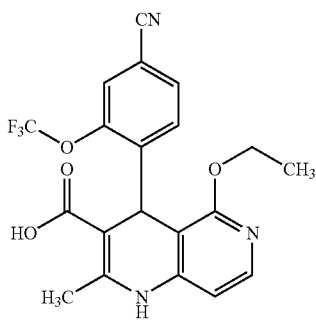 [SMILES: CCOc1nccc2c1C(c1ccc(C#N)cc1OC(F)(F)F)C(C(=O)O)=C(C)N2]

1400 mg (2.96 mmol) of the compound from Example 36A are dissolved in 35 ml of 1,2-dimethoxyethane/water (2.5:1 v/v), 5.93 ml (5.93 mmol) of 1 N sodium hydroxide solution are added, and the mixture is stirred at room temperature for 2 h. The reaction mixture is then mixed with 50 ml of diethyl ether and 50 ml of water. The aqueous phase is separated off and adjusted to a pH of 4-5 with 1 N hydrochloric acid. The resulting suspension is then stirred for 1 h. The resulting precipitate is filtered off and washed with water and a little diethyl ether. Drying in vacuo results in 850 mg (68% of theory) of the title compound.

LC-MS (method 3): $R_t$=2.19 min; MS (Elpos): m/z=420 [M+H]$^+$ $^1$H-NMR (300 MHz, DMSO-d$_6$): δ=1.11 (t, 3H), 2.31 (s, 3H), 4.06 (m, 1H), 4.13 (m, 1H), 5.37 (s, 1H), 6.49 (d, 1H), 7.51 (d, 1H), 7.65-7.72 (m, 2H), 7.76 (d, 1H), 9.42 (s, 1H), 11.62 (s, 1H).

Example 38A 4-(4-Cyano-2-methoxyphenyl)-5-ethoxy-2-(trifluoromethyl)-1,4-dihydro-1,6-naphthyridine-3-carboxylic acid

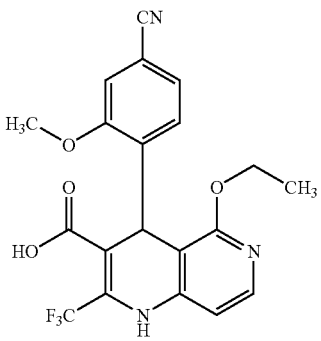

The title compound can be obtained starting from stoichiometric amounts of 4-formyl-3-methoxybenzonitrile (Example 10A), 4-aminopyridin-2(1H)-one [Searls, T., McLaughlin, L. W., Tetrahedron 55, 11985-11996 (1999)] and allyl 4,4,4-trifluoro-3-oxobutanoate [Moseley, J. D., Tetrahedron Lett. 46, 3179-3181 (2005)]. This entails firstly the dihydropyridine synthesis being carried out in ethanol without addition of additives at the reflux temperature overnight. The initially resulting intermediate allyl 4-(4-cyano-2-methoxyphenyl)-2-hydroxy-5-oxo-2-(trifluoromethyl)-1,2,3,4,5,6-hexahydro-1,6-naphthyridine-3-carboxylate can then be dehydrated with acetic acid in a literature-based process [cf. Moseley, J. D., Tetrahedron Lett. 46, 3179-3181 (2005)]. Subsequently, allyl 4-(4-cyano-2-methoxyphenyl)-5-ethoxy-2-(trifluoromethyl)-1,4-dihydro-1,6-naphthyridine-3-carboxylate can be obtained by reaction with triethyl orthoformate in analogy to the synthesis of Example 29A. Final allyl ester cleavage using Wilkinson's catalyst [tris(triphenylphosphine)rhodium(I) chloride] in acetic acid affords the title compound [cf. Moseley, J. D., Tetrahedron Lett. 46, 3179-3181 (2005)].

LC-MS (method 7): $R_t$=2.98 min; MS (Elpos): m/z=420 [M+H]$^+$ $^1$H-NMR (300 MHz, DMSO-d$_6$): δ=1.09 (t, 3H), 3.77 (s, 3H), 3.98-4.16 (m, 2H), 5.37 (s, 1H), 6.73 (d, 1H), 7.19 (d, 1H), 7.34 (dd, 1H), 7.42 (d, 1H), 7.78 (d, 1H), 9.62 (s, 1H).

Example 39A

2-Cyanoethyl 2,8-dimethyl-4-(2-methyl-4-oxo-4H-chromen-8-yl)-5-oxo-1,4,5,6-tetrahydro-1,6-naphthyridine-3-carboxylate

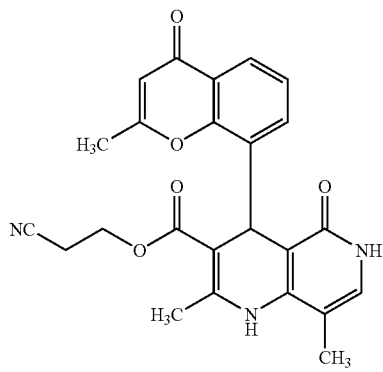

1.50 g (7.97 mmol) of the compound from Example 5A, 1.86 g (9.57 mmol) of 2-cyanoethyl 3-oxobutanoate [Yamamoto, T., et al., Bioorg. Med. Chem. Lett. 16, 798-802 (2006)], 91 μl (1.59 mmol) of acetic acid and 158 μl (1.59 mmol) of piperidine are dissolved in 30 ml of anhydrous dichloromethane and stirred under reflux with a water trap overnight. The mixture is then washed with water, the organic phase is dried with magnesium sulfate, and the volatile components are removed in a rotary evaporator. 2.91 g (approx. 7.33 mmol) of the 2-cyanoethyl (2Z)-2-[(2-methyl-4-oxo-4H-chromen-8-yl)methylidene]-3-oxobutanoate crude product obtained in this way are mixed with 0.990 g (9.00 mmol) of 4-amino-5-methylpyridin-2(1H)-one [Bisagni, E., Hung, N. C., *Synthesis,* 765-766 (1984)], taken up in 40 ml of 2-propanol and stirred at the reflux temperature overnight. After cooling, the resulting precipitate is filtered off and washed with a little diethyl ether. Drying under high vacuum results in 1.20 g (38% of theory) of the title compound.

LC-MS (method 8): $R_t$=1.00 min; MS (Elpos): m/z=432 [M+H]$^+$ $^1$H-NMR (300 MHz, DMSO-d$_6$): δ=2.06 (s, 3H), 2.34 (s, 3H), 2.44 (s, 3H), 2.77 (m, 2H), 3.98-4.14 (m, 2H), 5.76 (s, 1H), 6.15 (s, 1H), 6.98 (s, 1H), 7.28 (t, 1H), 7.71 (dd, 1H), 7.78 (dd, 1H), 8.29 (s, 1H), 10.78 (br. s, 1H).

Example 40A

2-Cyanoethyl 5-ethoxy-2,8-dimethyl-4-(2-methyl-4-oxo-4H-chromen-8-yl)-1,4-dihydro-1,6-naphthyridine-3-carboxylate

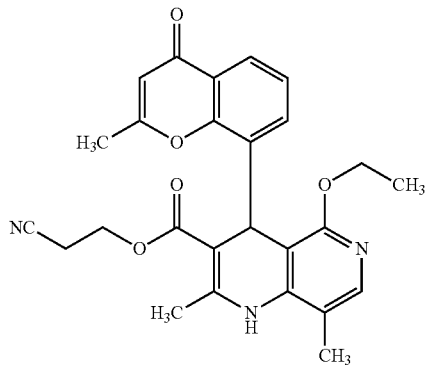 [SMILES: CCOc1ncc(C)c2c1C(c1cccc3c(=O)cc(C)oc13)C(C(=O)OCCC#N)=C(C)N2]

1.20 g (2.78 mmol) of the compound from Example 39A and 9.25 ml (55.6 mmol) of triethyl orthoformate are taken up in 30 ml of dry DMF and heated to 130° C., and 5 drops of concentrated sulfuric acid are added. After 2 h, an HPLC check shows complete conversion. After cooling, the volatile components are removed in a rotary evaporator, and the crude product is purified by MPLC (Biotage cartridge 40 M, eluent: isohexane/ethyl acetate 1:2). 640 mg (50% of theory) of the title compound are obtained.

LC-MS (method 9): $R_t$=0.99 min; MS (Elpos): m/z=460 [M+H]$^+$ $^1$H-NMR (300 MHz, DMSO-d$_6$): δ=1.01 (t, 3H), 2.19 (s, 3H), 2.38 (s, 3H), 2.48 (s, 3H), 2.75 (m, 2H), 3.93-4.14 (m, 4H), 5.55 (s, 1H), 6.18 (s, 1H), 7.30 (t, 1H), 7.63 (s, 1H), 7.67 (dd, 1H), 7.79 (dd, 1H), 8.49 (s, 1H).

Example 41A

5-Ethoxy-2,8-dimethyl-4-(2-methyl-4-oxo-4H-chromen-8-yl)-1,4-dihydro-1,6-naphthyridine-3-carboxylic acid

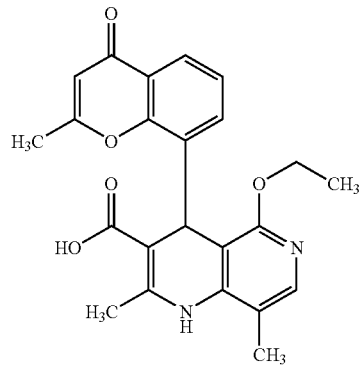 [SMILES: CCOc1ncc(C)c2c1C(c1cccc3c(=O)cc(C)oc13)C(C(=O)O)=C(C)N2]

640 mg (1.39 mmol) of the compound from Example 40A are dissolved in 30 ml of 1,2-dimethyoxyethane/water (2:1 v/v), mixed with 2.76 ml (2.76 mmol) of 1 N sodium hydroxide solution and stirred at room temperature for 30 min. The reaction mixture is then mixed with 20 ml of diethyl ether. The aqueous phase is separated off, adjusted to a pH of 4-5 with 1 N hydrochloric acid and extracted three times with ethyl acetate. The organic phases are combined and dried with magnesium sulfate. The volatile components are removed in a rotary evaporator. Drying in vacuo results in 335 mg (56% of theory) of the title compound in a purity of 94% (LC-MS).

LC-MS (method 8): $R_t$=1.21 min; MS (Elpos): m/z=407 [M+H]$^+$ $^1$H-NMR (300 MHz, DMSO-d$_6$): δ=1.01 (t, 3H), 2.18 (s, 3H), 2.35 (s, 3H), 2.42 (s, 3H), 3.90-4.10 (m, 2H), 5.54 (s, 1H), 6.18 (s, 1H), 7.31 (t, 1H), 7.58 (dd, 1H), 7.60 (s, 1H), 7.78 (dd, 1H), 8.25 (s, 1H), 11.52 (br. s, 1H).

Exemplary Embodiments

Example 1

4-(4-Cyano-2-methoxyphenyl)-5-ethoxy-2-methyl-1,4-dihydro-1,6-naphthyridine-3-carboxamide

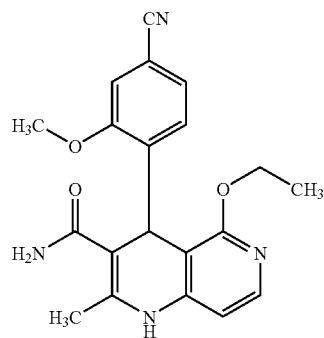

100 mg (approx. 0.24 mmol) of the compound from Example 23A are introduced into 3 ml of DMF. Then 2.94 mg (0.024 mmol) of 4-N,N-dimethylaminopyridine and 340 μl of ammonia (28% by weight solution in water, 2.41 mmol) are added, and the mixture is heated at 100° C. for 3 h. After cooling, the crude product is directly purified by preparative HPLC (eluent: acetonitrile/water with 0.1% formic acid, gradient 20:80→95:5). 32 mg (37% of theory) of the title compound are obtained.

LC-MS (method 3): $R_t$=1.57 min; MS (EIpos): m/z=365 [M+H]$^+$ $^1$H-NMR (300 MHz, DMSO-d$_6$): δ=1.07 (t, 3H), 2.13 (s, 3H), 3.83 (s, 3H), 4.04 (m, 2H), 5.36 (s, 1H), 6.42 (d, 1H), 6.66 (br. s, 2H), 7.18 (d, 1H), 7.29 (dd, 1H), 7.38 (d, 1H), 7.67 (d, 1H), 8.80 (s, 1H).

Example 2

4-(4-Cyano-2-methoxyphenyl)-5-ethoxy-2,7-dimethyl-1,4-dihydro-1,6-naphthyridine-3-carboxamide

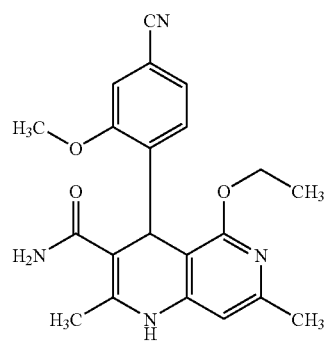 [SMILES: CCOc1nc(C)cc2c1C(c1ccc(C#N)cc1OC)C(C(N)=O)=C(C)N2]

640 mg (1.69 mmol) of the compound from Example 27A are introduced into 30 ml of ethyl acetate and, after addition of 342 mg (2.11 mmol) of 1,1'-carbonyldiimidazole, stirred at room temperature overnight. A TLC check (silica gel; mobile phase: cyclohexane/ethyl acetate 1:1 or dichloromethane/methanol 9:1) shows complete conversion. The volatile components are removed in a rotary evaporator, and the residue is taken up in 20 ml of DMF. Then 2.36 ml of ammonia (28% by weight solution in water, 16.87 mmol) are added, and the reaction mixture is heated at 50° C. for 8 h. The solvent is distilled out under reduced pressure, and the residue is purified by preparative HPLC (eluent: acetonitrile/water with 0.1% formic acid, gradient 20:80→95:5). 368 mg (58% of theory) of the title compound are obtained.

LC-MS (method 7): $R_t$=1.91 min; MS (EIpos): m/z=379 [M+H]$^+$ $^1$H-NMR (300 MHz, DMSO-d$_6$): δ=1.05 (t, 3H), 2.13 (s, 3H), 2.19 (s, 3H), 3.84 (s, 3H), 4.02 (q, 2H), 5.32 (s, 1H), 6.25 (s, 1H), 6.62 (br. s, 2H), 7.16 (d, 1H), 7.28 (dd, 1H), 7.37 (d, 1H), 8.71 (s, 1H).

Example 3 ent-4-(4-Cyano-2-methoxyphenyl)-5-ethoxy-2,7-dimethyl-1,4-dihydro-1,6-naphthyridine-3-carboxamide[(−)-enantiomer and (+)-enantiomer]

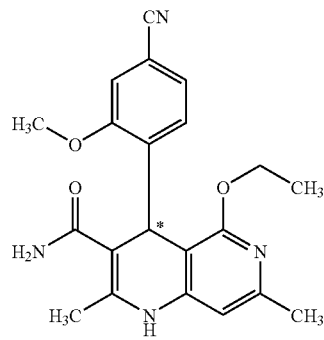 [SMILES: CCOc1nc(C)cc2c1C(c1ccc(C#N)cc1OC)C(C(N)=O)=C(C)N2]

The racemate from Example 2 can be fractionated into its enantiomers on the preparative scale by chiral phase HPLC [column: Chiralpak IA, 250 mm×20 mm; eluent: methyl tert-butyl ether/methanol 85:15 (v/v); flow rate: 15 ml/min; temperature: 30° C.; UV detection: 220 nm].

(−)-Enantiomer:
HPLC: $R_t$=5.28 min, ee>98% [column: Chiralpak IA, 250 mm×4.6 mm; eluent: methyl tert-butyl ether/methanol 80:20 (v/v); flow rate: 1 ml/min; temperature: 25° C.; UV detection: 220 nm];
specific rotation (chloroform, 589 nm, 19.8° C., c=0.50500 g/100 ml): −239.3°.

A single crystal X-ray structural analysis revealed an S configuration at the C* atom for this enantiomer.

(+)-Enantiomer:
HPLC: $R_t$=4.50 min, ee>99% [column: Chiralpak IA, 250 mm×4.6 mm; eluent: methyl tert-butyl ether/methanol 80:20 (v/v); flow rate: 1 ml/min; temperature: 25° C.; UV detection: 220 nm];
specific rotation (chloroform, 589 nm, 20° C., c=0.51000 g/100 ml): +222.7°.

Example 4

4-(4-Cyano-2-methoxyphenyl)-5-ethoxy-2,8-dimethyl-1,4-dihydro-1,6-naphthyridine-3-carboxamide

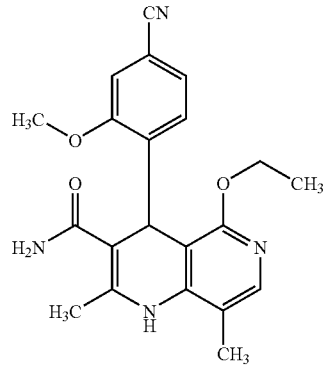 [SMILES: CCOc1ncc(C)c2c1C(c1ccc(C#N)cc1OC)C(C(N)=O)=C(C)N2]

1.46 g (3.84 mmol) of the compound from Example 30A are introduced into 50 ml of ethyl acetate and, after addition of 777 mg (4.79 mmol) of 1,1'-carbonyldiimidazole, stirred at room temperature overnight. A TLC check (silica gel; mobile phase: ethyl acetate) shows complete conversion. The volatile components are removed in a rotary evaporator, and the residue is taken up in 20 ml of DMF. Then 10.74 ml of ammonia (28% by weight solution in water, 76.8 mmol) are added, and the reaction mixture is heated at 100° C. for 30 min. The solvent is distilled out under reduced pressure, and the residue is purified by preparative HPLC (eluent: acetonitrile/water with 0.1% formic acid, gradient 20:80→95:5). The residue after concentration of the product fractions is dissolved in 40 ml of dichloromethane/methanol (1:1 v/v) and mixed with 100 ml of ethyl acetate. The solvent is concentrated to a volume of about 20 ml, whereupon the product crystallizes. The precipitate is filtered off and washed with a little diethyl ether. Drying at 40° C. in a vacuum drying oven results in 1.40 g (96% of theory) of the title compound.

LC-MS (method 3): $R_t$=1.64 min; MS (EIpos): m/z=379 [M+H]$^+$ $^1$H-NMR (300 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Example 5 ent-4-(4-Cyano-2-methoxyphenyl)-5-ethoxy-2,8-dimethyl-1,4-dihydro-1,6-naphthyridine-3-carboxamide[(−)-enantiomer and (+)-enantiomer]

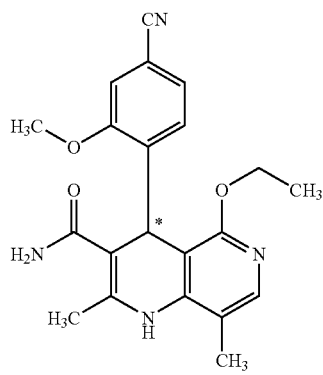 [SMILES: CCOc1ncc(C)c2c1C(c1ccc(C#N)cc1OC)C(C(N)=O)=C(C)N2]

The racemate from Example 4 can be fractionated into its enantiomers on the preparative scale by chiral phase HPLC [column: 680 mm×40 mm; silica gel phase based on the chiral selector poly(N-methacryloyl-D-leucine-dicyclopropylmethylamide; eluent: ethyl acetate; temperature: 24° C.; flow rate: 80 ml/min; UV detection: 260 nm].

(−)-Enantiomer:
HPLC: $R_t$=2.48 min, ee=99.6% [column: 250 mm×4.6 mm; silica gel phase based on the chiral selector poly(N-methacryloyl-D-leucine-dicyclopropylmethylamide; eluent: ethyl acetate; temperature: 24° C.; flow rate: 2 ml/min; UV detection: 260 nm];

specific rotation (chloroform, 589 nm, 19.7° C., c=0.38600 g/100 ml): −148.8°.

A single crystal X-ray structural analysis revealed an S configuration at the C* atom for this enantiomer.

(+)-Enantiomer:
HPLC: $R_t$=4.04 min, ee=99.3% [column: 250 mm×4.6 mm; silica gel phase based on the chiral selector poly(N-methacryloyl-D-leucine-dicyclopropylmethylamide; eluent: ethyl acetate; temperature: 24° C.; flow rate: 2 ml/min; UV detection: 260 nm];

specific rotation (chloroform, 589 nm, 19.8° C., c=0.36300 g/100 ml): +153.0°.

Example 6

5-Ethoxy-2-methyl-4-(2-methyl-4-oxo-4H-chromen-8-yl)-1,4-dihydro-1,6-naphthyridine-3-carboxamide

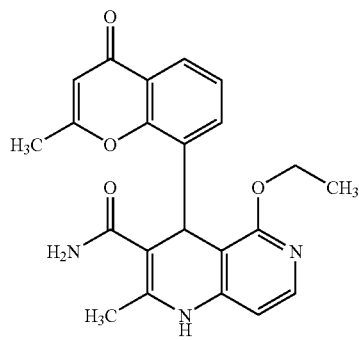 [SMILES: CCOc1nccc2c1C(c1cccc3c(=O)cc(C)oc13)C(C(N)=O)=C(C)N2]

155 mg (0.395 mmol) of the compound from Example 31A are introduced into 10 ml of THF and, after addition of 80.1 mg (0.494 mmol) of 1,1'-carbonyldiimidazole, stirred at room temperature overnight. A TLC check (silica gel; mobile phase: ethyl acetate or dichloromethane/methanol 9:1) shows complete conversion. The volatile components are removed in a rotary evaporator, and the residue is taken up in 3 ml of DMF. Then 553 mg of ammonia (28% by weight solution in water, 3.95 mmol) are added, and the reaction mixture is heated at 100° C. for 10 min. The solvent is removed under reduced pressure, and the residue is purified by preparative HPLC (eluent: acetonitrile/water with 0.1% formic acid, gradient 20:80→95:5). 30 mg (19% of theory) of the title compound are obtained.

LC-MS (method 6): $R_t$=1.17 min; MS (EIpos): m/z=392 [M+H]$^+$ $^1$H-NMR (300 MHz, DMSO-d$_6$): δ=0.96 (t, 3H), 2.09 (s, 3H), 2.36 (s, 3H), 3.94 (m, 1H), 4.03 (m, 1H), 5.59 (s, 1H), 6.19 (s, 1H), 6.42 (d, 1H), 6.66 (br. s, 1H), 7.00 (br. s, 1H), 7.31 (t, 1H), 7.53 (dd, 1H), 7.68 (d, 1H), 7.79 (dd, 1H), 8.83 (s, 1H).

Example 7

4-[4-Cyano-2-(trifluoromethoxy)phenyl]-5-ethoxy-2-methyl-1,4-dihydro-1,6-naphthyridine-3-carboxamide

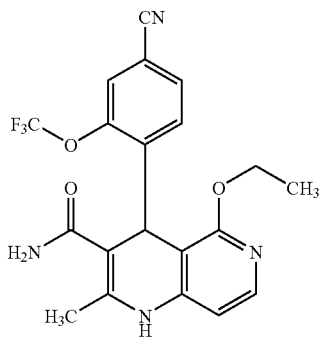 [SMILES: CCOc1nccc2c1C(c1ccc(C#N)cc1OC(F)(F)F)C(C(N)=O)=C(C)N2]

200 mg (0.477 mmol) of the compound from Example 37A are introduced into 5 ml of ethyl acetate and, after addition of 96.7 mg (0.596 mmol) of 1,1'-carbonyldiimidazole, stirred at room temperature overnight (TLC check: insufficient reaction). Then 1 ml of DMF is added, and the mixture is stirred at room temperature for a further night (TLC check: complete conversion). The volatile components are removed in a rotary evaporator, and the residue is taken up in 4 ml of DMF. Then 663 μl of ammonia (28% by weight solution in water, 4.77 mmol) are added, and the reaction mixture is heated at 100° C. in a closed vessel overnight. After cooling, the solvent is removed under reduced pressure, and the residue is purified by preparative HPLC (eluent: acetonitrile/water with 0.1% formic acid, gradient 20:80→95:5). 140 mg (70% of theory) of the title compound are obtained.

LC-MS (method 6): $R_t$=2.26 min; MS (Elpos): m/z=419 [M+H]$^+$ $^1$H-NMR (300 MHz, DMSO-d$_6$): δ=1.04 (t, 3H), 2.04 (s, 3H), 4.06 (m, 2H), 5.42 (s, 1H), 6.41 (d, 1H), 6.80 (br. s, 1H), 6.97 (br. s, 1H), 7.45 (d, 1H), 7.68-7.74 (m, 3H), 8.82 (d, 1H).

Example 8

4-(4-Cyano-2-methoxyphenyl)-5-ethoxy-2-(trifluoromethyl)-1,4-dihydro-1,6-naphthyridine-3-carboxamide

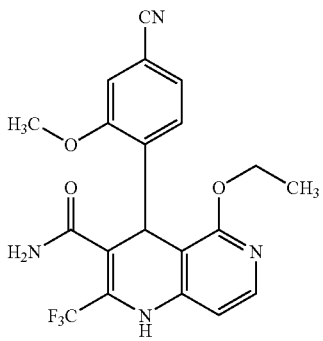 [SMILES: CCOc1nccc2c1C(c1ccc(C#N)cc1OC)C(C(N)=O)=C(C(F)(F)F)N2]

180 mg (0.429 mmol) of the compound from Example 38A are introduced into 5 ml of ethyl acetate and, after addition of 87.0 mg (0.537 mmol) of 1,1'-carbonyldiimidazole, stirred at room temperature for two hours. Complete conversion is established by a TLC check. The volatile components are removed in a rotary evaporator, and the residue is taken up in 4 ml of DMF. Then 597 μl of ammonia (28% by weight solution in water, 4.29 mmol) are added, and the reaction mixture is heated at 100° C. in a closed vessel for three hours. After cooling, the solvent is removed under reduced pressure, and the residue is purified by preparative HPLC (eluent: acetonitrile/water with 0.1% formic acid, gradient 20:80→95:5). 10 mg (5% of theory) of the title compound are obtained.

LC-MS (method 3): $R_t$=1.85 min; MS (Elpos): m/z=419 [M+H]$^+$ $^1$H-NMR (300 MHz, DMSO-d$_6$): δ=1.03 (t, 3H), 3.79 (s, 3H), 3.96-4.11 (m, 2H), 5.37 (s, 1H), 6.62 (d, 1H), 7.08-7.14 (m, 2H), 7.32 (dd, 1H), 7.37-7.46 (m, 2H), 7.73 (d, 1H), 9.18 (s, 1H).

Example 9

5-Ethoxy-2,8-dimethyl-4-(2-methyl-4-oxo-4H-chromen-8-yl)-1,4-dihydro-1,6-naphthyridine-3-carboxamide

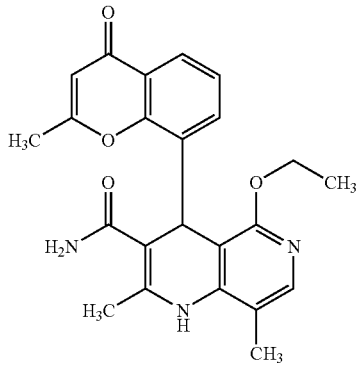 [SMILES: CCOc1ncc(C)c2c1C(c1cccc3c(=O)cc(C)oc13)C(C(N)=O)=C(C)N2]

335.0 mg (0.824 mmol) of the compound from Example 41A are introduced into 10 ml of ethyl acetate, and 167.1 mg (0.537 mmol) of 1,1'-carbonyldiimidazole are added. The suspension is then stirred at room temperature overnight. Since a clear solution is not produced, 2 ml of DMF are added and the mixture is stirred at room temperature for a further two hours. Complete conversion is then established by TLC check. The volatile components are removed in a rotary evaporator, and the residue is taken up in 4 ml of DMF. Then 2.293 ml of ammonia (28% by weight solution in water, 16.5 mmol) and 10.1 mg of 4-N,N-dimethylaminopyridine are added. The reaction mixture is heated at 100° C. in a closed vessel for thirty minutes. After cooling, the solvent is removed under reduced pressure, and the residue is purified by preparative HPLC (eluent: acetonitrile/water with 0.1% formic acid, gradient 20:80→95:5). The product fractions are concentrated and the residue is taken up in a little dichloromethane, and diisopropyl ether is added until the solution is cloudy. The precipitated solid is isolated and dried in vacuo. 207 mg (59% of theory) of the title compound are obtained.

LC-MS (method 9): $R_t$=0.67 min; MS (Elpos): m/z=406 [M+H]$^+$ $^1$H-NMR (300 MHz, DMSO-d$_6$): δ=0.94 (t, 3H), 2.13 (s, 3H), 2.14 (s, 3H), 2.34 (s, 3H), 3.90 (m, 1H), 4.00 (m, 1H), 5.58 (s, 1H), 6.18 (s, 1H), 6.70 (br. s, 1H), 7.06 (br. s, 1H), 7.30 (t, 1H), 7.50 (dd, 1H), 7.56 (s, 1H), 7.71 (s, 1H), 7.78 (dd, 1H).

B. ASSESSMENT OF THE PHARMACOLOGICAL ACTIVITY

Abbreviations:

| | |
|---|---|
| DMEM | Dulbecco's modified Eagle medium |
| DNA | deoxyribonucleic acid |
| FCS | fetal calf serum |
| HEPES | 4-(2-hydroxyethyl)-1-piperazineethanesulfonic acid |
| PCR | polymerase chain reaction |
| Tris | tris-(hydroxymethyl)methylamine |

The advantageous pharmacological properties of the compounds of the invention can be shown in the following assays:

1. Cellular In Vitro Assay to Determine the Inhibitory MR Activity and MR Selectivity Compared with Other Steroid Hormone Receptors Antagonists of the human mineralocorticoid receptor (MR) are identified, and the activity of the compounds described herein is quantified with the aid of a recombinant cell line. The cell is originally derived from a hamster ovary epithelial cell (Chinese Hamster Ovary, CHO K1, ATCC: American Type Culture Collection, VA 20108, USA).

An established chimera system in which the ligand-binding domains of human steroid hormone receptors are fused to the DNA-binding domain of the yeast transcription factor GAL4 is used in this CHO K1 cell line. The GAL4-steroid hormone receptor chimeras produced in this way are cotransfected and stably expressed with a reporter construct in the CHO cells.

Clonings:

To generate the GAL4-steroid hormone receptor chimeras, the GAL4 DNA binding domain (amino acids 1-147) from the vector pFC2-dbd (from Stratagene) is cloned with the PCR-amplified ligand-binding domains of the mineralocorticoid receptor (MR, amino acids 734-985), of the glucocorticoid receptor (GR, amino acids 443-777), of the progesterone receptor (PR, amino acids 680-933) and of the androgen receptor (AR, amino acids 667-919) into the vector pIRES2 (from Clontech). The reporter construct, which comprises five copies of the GAL4 binding site upstream of a thymidine kinase promoter, leads to expression of firefly-luciferase (*Photinus pyralis*) after activation and binding of the GAL4-steroid hormone receptor chimeras by the respective specific agonists aldosterone (MR), dexamethasone (GR), progesterone (PR) and dihydrotestosterone (AR).

Assay Procedure:

The MR, GR, PR and AR cells are plated out in medium (Optimem, 2.5% FCS, 2 mM glutamine, 10 mM HEPES) in 96- (or 384- or 1536-) well microtiter plates on the day before the assay and are kept in a cell incubator (96% humidity, 5% v/v $CO_2$, 37° C.). On the day of the assay, the substances to be tested are taken up in the abovementioned medium and added to the cells. About 10 to 30 minutes after addition of the test substances, the respective specific agonists of the steroid hormone receptors are added. After a further incubation time of 5 to 6 hours, the luciferase activity is measured with the aid of a video camera. The measured relative light units as a function of the substance concentration result in a sigmoidal stimulation curve. The $IC_{50}$ values are calculated with the aid of the GraphPad PRISM computer program (Version 3.02).

Table A shows the $IC_{50}$ values (MR) of representative exemplary compounds:

TABLE A

| Example No. | MR $IC_{50}$ [nM] |
|---|---|
| 1 | 35 |
| 4 | 23 |
| 5 | 16 |
| [(−)-enantiomer] | |

2. In Vitro Assay to Determine Possible Binding Activity to the L-Type Calcium Channel Membrane preparations of the cerebral cortex of Wistar rats serve as starting material for a radioactive binding assay which is described in detail in the literature as standard assay [Ehlert, F. J., Roeske, W. R., Itoga E., Yamamura, H. I., *Life Sci.* 30, 2191-2202 (1982); Gould, R. J., Murphy, K. M. M., Snyder, S. H., *Proc. Natl. Acad. Sci. U.S.A.* 79, 3656-3660] and is used in contract investigations by commercial service suppliers (e.g. MDS Pharma Services). In this binding assay, serial dilutions of the test compounds in DMSO are incubated with the membrane preparations and the tritium-labeled ligand nitrendipine (0.1 nM) in a 50 mM TrisHCl buffer, pH 7.7, at 25° C. typically for 90 minutes, and the specific binding of the test compounds is determined by quantifying the specifically displaced, radiolabelled ligand. $IC_{50}$ values are determined by a nonlinear regression analysis.

The $IC_{50}$ value determined in this L-type calcium channel binding assay for a conventional calcium antagonist of the dihydropyridine type such as, for example, nitrendipine is 0.3 nM, whereas the $IC_{50}$ values for investigated examples of the compounds of the invention described herein are >1 μM and thus the affinity shown for the L-type calcium channel is reduced by a factor of at least 3000. Compounds with such a low residual binding affinity for the L-type calcium channel no longer show pronounced hemodynamic effects mediated by the L-type calcium channel in vivo.

3. In Vivo Assay for Detecting the Cardiovascular Effect: Diuresis Investigations on Conscious Rats in Metabolism Cages Wistar rats (bodyweight 250-350 g) are kept with free access to feed (Altromin) and drinking water. From about 72 hours before the start of the test, the animals receive instead of the normal feed exclusively salt-reduced feed with a sodium chloride content of 0.02% (ssniff R/M–H, 10 mm with 0.02% Na, 50602-E081, ssniff Spezialdiaten GmbH, D-59494 Soest). During the test, the animals are housed singly in metabolism cages suitable for rats of this weight class (from Tecniplast Germany GmbH, D-82383 Hohenpeißenberg) with free access to salt-reduced feed and drinking water for about 24 hours. At the start of the test, the substance to be tested is administered into the stomach by means of gavage in a volume of 0.5 ml/kg of bodyweight of a suitable solvent. Control animals receive only solvent. Controls and substance tests are carried out in parallel on the same day. Control groups and substance-dose groups each consist of 3 to 6 animals. During the test, the urine excreted by the animals is continuously collected in a receiver on the base of the cage. The urine volume per unit time is determined separately for each animal, and the concentration of the sodium and potassium ions excreted in the urine is measured by standard methods of flame photometry. The sodium/potassium ratio is calculated from the measurements as a measure of the effect of the substance. The measurement intervals are typically the period up to 8 hours after the start of the test (day interval) and the period from 8 to 24 hours after the start of the test (night interval). In a modified test design, the urine is collected and measured at intervals of two hours during the day interval. In order to obtain a sufficient amount of urine for this purpose, the animals receive a defined amount of water by gavage at the start of the test and then at intervals of two hours.

4. DOCA/Salt Model

Administration of deoxycorticosterone acetate (DOCA) in combination with a high-salt diet and unilateral kidney removal in rats induces hypertension which is characterized by relatively low renin levels. As a consequence of this endocrine hypertension (DOCA is a direct precursor of aldosterone), there is, depending on the chosen DOCA concentration, cardiac hypertrophy and further end organ damage, e.g. of the kidney, which is characterized inter alia by protein urea and glomerulosclerosis. It is thus possible to investigate test substances in this rat model for the presence of an antihypertrophic and end organ-protecting effect.

Approximately 8-week old (body weight between 250 and 300 grams) male Sprague-Dawley (SD) rats undergo left uninephrectomy. For this purpose, the rats are anesthetized with 1.5-2% isoflurane in a mixture of 66% $N_2O$ and 33% $O_2$, and the kidney is removed through a flank incision. So-called sham-operated animals from which no kidney is removed serve as later control animals.

Uninephrectomized SD rats receive 1% sodium chloride in the drinking water and a subcutaneous injection of deoxycorticosterone acetate (dissolved in sesame oil; from Sigma) injected between the shoulder blades once a week (high dose: 100 mg/kg/week s.c.; normal dose: 30 mg/kg/week s.c.).

The substances which are to be investigated for their protective effect in vivo are administered by gavage or via the feed (from Ssniff). One day before the start of the test, the animals are randomized and assigned to groups with an identical number of animals, usually n=10, Throughout the test, drinking water and feed are available ad libitum to the animals. The substances are administered via the feed or once a day by gavage for 4-8 weeks Animals serving as placebo group are treated in the same way but receive either only the solvent or the feed without test substance.

The effect of the test substances is determined by measuring hemodynamic parameters [blood pressure, heart rate, inotropism (dp/dt), relaxation time (tau), maximum left ventricular pressure, left-ventricular end-diastolic pressure (LVEDP)], determining the weight of the heart, kidney and lung, measuring the protein excretion, and by measuring gene expression of biomarkers (e.g. ANP, atrial natriuretic peptide, and BNP, brain natriuretic peptide) by means of RT/TaqMan PCR after RNA isolation from cardiac tissue.

Statistical analysis takes place using Student's t test after previous examination of the variances for homogeneity.

5. In Vivo Assay for Detecting Anti-Mineralocorticoid Activity on Anesthetized Dogs Male or female mongrel dogs (mongrels, Marshall BioResources, USA) with a weight between 20 and 30 kilograms are anesthetized with pentobarbital (30 mg/kg intravenously; Narcoren®, Merial, Germany). Alcuronium chloride (3 mg/animal intravenously; Alloferin®, ICN Pharmaceuticals, Germany) is used in addition as muscle relaxant. The dogs are intubated and ventilated with an oxygen/ambient air mixture (40/60 Vol.-%) (about 5-6 liters/min). The ventilation takes place with a ventilator supplied by Draeger (Sulla 808) and is monitored with a $CO_2$ analyzer (from Engstrom). The anesthesia is maintained by continuous infusion of pentobarbital (50 µg/kg/min) or isoflurane (1-2 Vol.-%). Fentanyl (10 µg/kg/h) is used as analgesic.

The primary aim of the test is to investigate the effect of test compounds with antimineralocorticoid receptor activity on the aldosterone-induced sodium retention. The procedure for this is analogous to a published method [H. P. Ramjoe, U. M. Bucher, J. Richter und M. De Gasparo, *Anti-mineralocorticoid activity of three novel aldosterone antagonists in the conscious dog and in man*, in: *Diuretics II: Chemistry, Pharmacology, and Clinical Applications*, J. B. Puschett und A. Greenberg (Ed.), Elsevier Science Publishing Co., Inc., 1987]. A continuous infusion of aldosterone (0.6 µg/kg/h) leads after 3 hours to a decrease in the sodium/potassium ratio in the urine (sodium and potassium are determined by flame photometry). The test substance is administered intravenously, intraduodenally or orally, continuing the aldosterone infusion. Spironolactone is used as positive control and increases the sodium/potassium ratio in the urine dose-dependently.

To ensure constant hemodynamics and to measure functional cardiovascular parameters, the dog undergoes hemodynamic monitoring and instrumentation in the following way:

introduction of a bladder catheter to measure the urine flow and the urine composition;

attachment of ECG leads to the extremities for ECG measurement;

introduction into the femoral artery of a Fluidmedic PE 300 tube which is filled with saline and which is connected to a pressure sensor (from Braun, Melsungen, Germany) for measuring the systemic blood pressure;

introduction of a Millar Tip catheter (type 350 PC, Millar Instruments, Houston, USA) through the left atrium or through a port secured in the carotid artery for measuring cardiac hemodynamics;

introduction of a Swan-Ganz catheter (CCOmbo 7.5F, Edwards, Irvine, USA) via the jugular vein into the pulmonary artery to measure the cardiac output, oxygen saturation, pulmonary arterial pressures and central venous pressure;

attachment of an ultrasonic flow measuring probe (Transsonic Systems, Ithaca, USA) to the descending aorta to measure the aortic flow;

attachment of an ultrasonic flow measuring probe (Transsonic Systems, Ithaca, USA) to the left coronary artery to measure the coronary flow;

siting a Braunüle in the cephalic vein for infusing pentobarbital, liquid replacement and for blood sampling (determination of the plasma levels of substance or other clinical blood parameters);

siting of a Brauüle in the saphenous vein, for fentanyl and aldosterone infusion and for administration of substance.

The primary signals are amplified if necessary (Gould amplifier, Gould Instrument Systems, Valley View, USA or Edwards Vigilance-Monitor, Edwards, Irvine, USA) and subsequently fed into the Ponemah system (DataSciences Inc., Minneapolis, USA) for analysis. The signals are recorded continuously throughout the test period, further processed digitally by this software and averaged over 30 seconds.

6. Chronic Myocardial Infarction Model in Concious Rats

Male Wistar rats (280-300 g body weight; Harlan-Winkelmann) are anesthetized with 5% isoflurane in an anesthesia cage, connected to a ventilation pump (ugo basile 7025 rodent, 50 strokes/min, 7 ml) and ventilated with 2% isoflurane/$N_2O$/$O_2$. The body temperature is maintained at 37-38° C. by a heating mat. 0.05 mg/kg Temgesic is given subcutaneously as analgesic. The chest is opened laterally between the third and fourth rib, and the heart is exposed. The coronary artery of the left ventricle (LAD) is permanently ligated with an occlusion thread (prolene 1 metric 5-0 ethicon1H) passed underneath shortly below its origin (below the left atrium). The occurrence of a myocardial infarction is monitored by an ECG measurement (Cardioline, Remco, Italy). The thorax is reclosed and the muscle layers are sutured with Ethibond excel 1 metric 5/0 6951H and the epidermis is sutured with Ethibond excel 3/0 6558H. The surgical suture is wetted with a spray dressing (e.g. Nebacetin®N in spray dressing, active ingredient: neomycin sulfate) and then the anesthesia is terminated.

One week after the LAD occlusion, the size of the myocardial infarct is estimated by echocardiography (Sequoia 512, Acuson). The animals are randomized and divided into individual treatment groups and a control group without substance treatment. A sham group in which only the surgical procedure, but not the LAD occlusion, was performed is included as further control.

Substance treatment takes place over 8 weeks by gavage or by adding the test compound to the feed or drinking water. The animals are weighed each week, and the water and feed consumption is determined every 14 days.

After treatment for 8 weeks, the animals are again anesthetized (2% isoflurane/$N_2O$/air) and a pressure catheter (Millar SPR-320 2F) is inserted via the carotid artery into the left ventricle. The heart rate, left ventricular pressure (LVP), left-ventricular end-diastolic pressure (LVEDP), contractility (dp/dt) and relaxation rate ($\tau$) are measured there and analyzed with the aid of the Powerlab systems (AD Instruments, ADI-PWLB-4SP) and the Chart 5 software (SN 425-0586). A blood sample is then taken to determine the blood levels of the substance and plasma biomarkers, and the animals are sacrificed. The heart (heart chambers, left ventricle with septum, right ventricle), liver, lung and kidney are removed and weighed.

7. Stroke-Prone Spontaneously Hypertensive Rat Model

Administration of sodium chloride to the so-called stroke-prone spontaneously hypertensive rat (SP-SHR) leads in this model paradoxically to abolition of the physiological salt-induced repression of renin and angiotensin release after a few days. Thus, the hypertension in the SP-SHR animals is characterized by a relatively high renin level. As a consequence of the developing hypertension there is pronounced end-organ damage to the heart and the kidney, which is characterized inter alia by proteinurea and glomerulosclerosis, and general vascular changes. Thus, in particular strokes may develop primarily through cerebrovascular lesions ("stroke-prone") which lead to a high mortality of the untreated animals. It is thus possible to investigate test substances for blood pressure-lowering and end organ-protecting effect in this rat model.

Approximately 10-week old male SP-SH rats (body weight between 190 and 220 g) are randomized and assigned to groups with an equal number of animals, usually n=12-14, one day before the start of the test. Throughout the test, drinking water containing sodium chloride (2% NaCl) and feed are available ad libitum to the animals. The substances are administered once a day by gavage or with the feed (Ss-niff, Germany) for 6-8 weeks Animals treated in the same way but receiving either only the solvent or the feed without test substance serve as placebo group. In the context of a mortality study, the test is terminated when about 50% of the placebo-treated animals have died.

The effect of the test substances is followed by measuring the changes in the systolic blood pressure (via a tail cuff) and the protein excretion in the urine. There are post mortem determinations of the weights of heart, kidney and lung, and histopathological analyses of the heart, kidney and brain with semiquantitative scoring of the histological changes. Various biomarkers (e.g. ANP, atrial natriuretic peptide, and BNP, brain natriuretic peptide, KIM-1, kidney-induced molecule 1, osteopontin-1) are determined by RT/TaqMan PCR following RNA isolation from cardiac and renal tissue or serum or plasma.

Statistical analysis is carried out with Student's t test after previous examination of the variances of homogeneity.

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Suspension which can be administered orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be administered orally:

Composition:

500 mg of the compound of the invention, 2.5 g of polysorbate and 97 g of polyethylene glycol 400. 20 g of oral solution correspond to a single dose of 100 mg of the compound according to the invention.

Production:

The compound of the invention is suspended in the mixture of polyethylene glycol and polysorbate with stirring. The stirring process is continued until the compound according to the invention has completely dissolved.

i.v. Solution:

The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:
1. A compound of the formula (I)

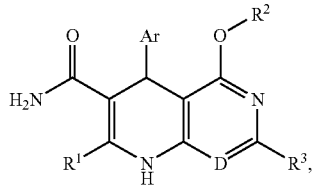

in which
D is N or C—R$^4$, in which
R$^4$ is hydrogen, fluorine, trifluoromethyl or (C$_1$-C$_4$)-alkyl,
Ar is a group of the formula

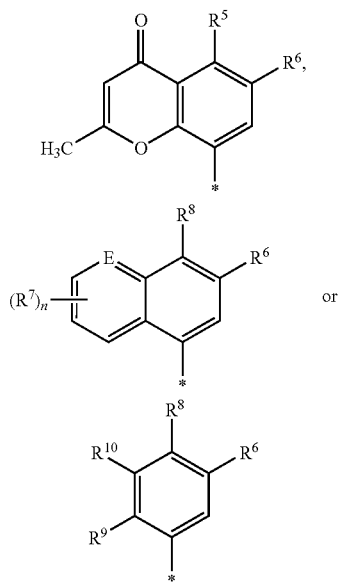

in which
* is the linkage point,
R$^5$ is hydrogen, fluorine, chlorine, cyano, nitro, trifluoromethyl or (C$_1$-C$_4$)-alkyl,
R$^6$ is hydrogen or fluorine,
R$^7$ is halogen, (C$_1$-C$_4$)-alkyl, trifluoromethyl, (C$_1$-C$_4$)-alkoxy or trifluoromethoxy,
R$^8$ is cyano or nitro,
R$^9$ is hydrogen, halogen, (C$_1$-C$_4$)-alkyl, (C$_1$-C$_4$)-alkoxy, (C$_1$-C$_4$)-alkylthio or di-(C$_1$-C$_4$)-alkylamino, it being possible for the alkyl group in said (C$_1$-C$_4$)-alkyl, (C$_1$-C$_4$)-alkoxy and (C$_1$-C$_4$)-alkylthio radicals in each case to be substituted up to three times by fluorine, or
phenyl, which may be substituted by halogen, (C$_1$-C$_4$)-alkyl or trifluoromethyl,
R$^{10}$ is hydrogen, halogen or (C$_1$-C$_4$)-alkyl,
E is CH, C—R$^7$ or N, and
n is the number 0, 1 or 2,
it being possible in the case where the substituent R$^7$ occurs more than once for its meanings to be identical or different,
R$^1$ is (C$_1$-C$_4$)-alkyl which may be substituted up to three times by fluorine,
R$^2$ is (C$_1$-C$_6$)-alkyl which may be substituted by (C$_3$-C$_7$)-cycloalkyl or up to three times by fluorine, or is a group of the formula —SO$_2$—R$^{11}$ in which
R$^{11}$ is (C$_1$-C$_6$)-alkyl, trifluoromethyl, (C$_3$-C$_7$)-cycloalkyl, phenyl or 5- or 6-membered heteroaryl having up to two heteroatoms from the series N, O and/or S,
it being possible for phenyl and heteroaryl in turn each to be substituted once or twice, identically or differently, by halogen, cyano, nitro, (C$_1$-C$_4$)-alkyl, trifluoromethyl, (C$_1$-C$_4$)-alkoxy and/or trifluoromethoxy,
and
R$^3$ is hydrogen, fluorine, trifluoromethyl or (C$_1$-C$_4$)-alkyl,
or a salt thereof.
2. A compound of the formula (I) as claimed in claim 1, in which
D is C—R$^4$ in which
R$^4$ is hydrogen, methyl or trifluoromethyl,
Ar is a group of the formula

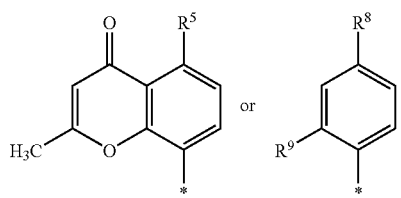

in which
* is the linkage point,
R$^5$ is hydrogen, fluorine, chlorine or cyano,
R$^8$ is cyano or nitro, and
R$^9$ is chlorine, bromine, (C$_1$-C$_4$)-alkyl, trifluoromethyl, (C$_1$-C$_4$)-alkoxy, trifluoromethoxy, (C$_1$-C$_4$)-alkylthio or trifluoromethylthio,
R$^1$ is methyl or trifluoromethyl,
R$^2$ is (C$_1$-C$_4$)-alkyl, trifluoromethyl or a group of the formula —SO$_2$—R$^{11}$ in which
R$^{11}$ is (C$_1$-C$_4$)-alkyl or trifluoromethyl, and
R$^3$ is hydrogen, methyl or trifluoromethyl,
or a salt thereof.
3. A compound of the formula (I) as claimed in claim 1, in which
D is C—R$^4$ in which
R$^4$ is hydrogen or methyl,
Ar is a group of the formula

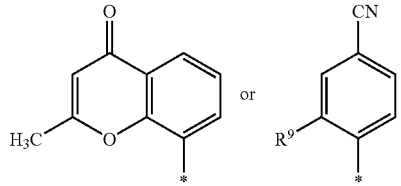

in which
* is the linkage point and
R$^9$ is ethyl, methoxy or trifluoromethoxy,
R$^1$ is methyl or trifluoromethyl,
R$^2$ is methyl, ethyl, n-propyl or isopropyl and $R^3$ is hydrogen or methyl,
or a salt thereof.
4. A compound as claimed in claim 1, having one of the following structures:
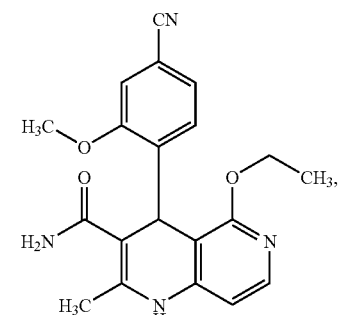
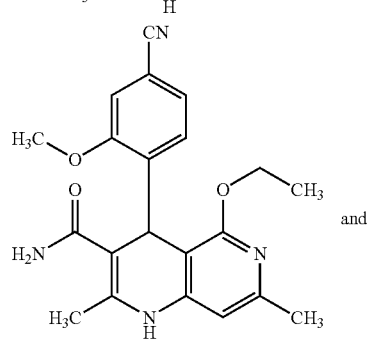
and
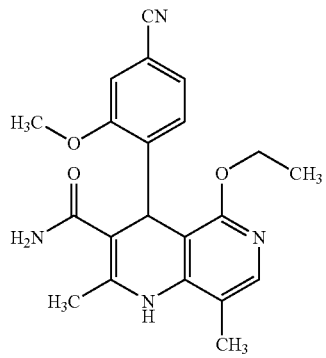
or a salt thereof.
5. A compound as claimed in claim 1, having one of the following structures:
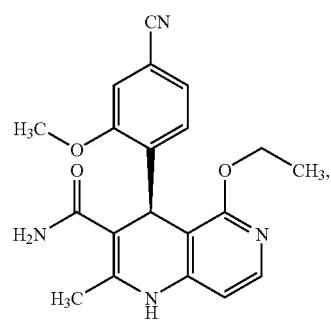
-continued
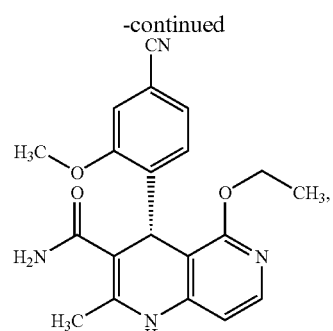
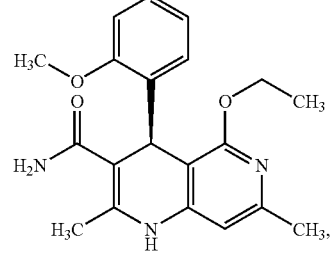
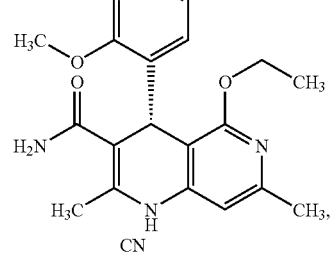
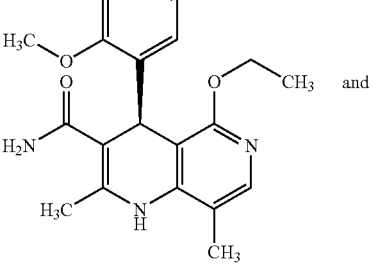
and
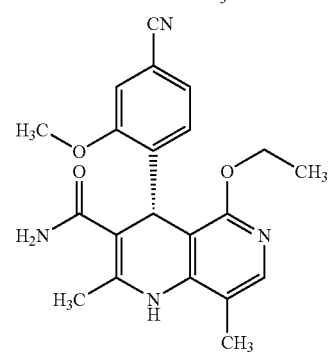
or a salt thereof.
6. A process for preparing compounds of the formula (I) as defined in claim 1, comprising reacting a compound of the formula (II)

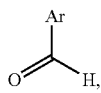
(II)

in which Ar has the meaning indicated in claim 1, in an inert solvent, optionally, in the presence of an acid, an acid/base combination and/or a dehydrating agent, with a compound of the formula (III)

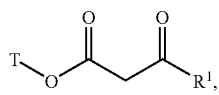
(III)

in which $R^1$ has the meaning indicated in claim 1, and
T is allyl or 2-cyanoethyl,
to give a compound of the formula (IV)

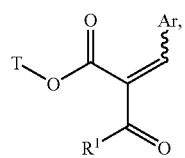
(IV)

in which Ar, T and $R^1$ each have the meanings indicated above,
condensing the compound of formula (IV) in an inert solvent with a compound of the formula (V)

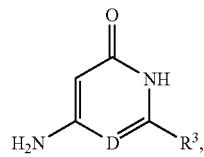
(V)

in which D and $R^3$ have the meanings indicated in claim 1, to give a compound of the formula (VI)

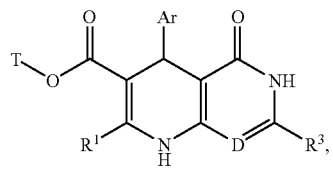
(VI)

in which Ar, D, T, $R^1$ and $R^3$ each have the meanings indicated above, alkylating a compounds of the formula (VI) in an inert solvent, optionally, in the presence of a base, with a compound of the formula (VII) or a trialkyloxonium salt of the formula (VIII)

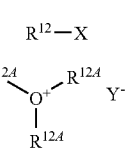

(VII)

(VIII)

in which
$R^{12}$ is $(C_1\text{-}C_6)$-alkyl which may be substituted by $(C_3\text{-}C_7)$-cycloalkyl or up to three times by fluorine,
$R^{12A}$ is methyl or ethyl,
X is a leaving group such as, for example, halogen, mesylate, tosylate or triflate, and
$Y^-$ is a non-nucleophilic anion such as, for example, tetrafluoroborate,
or in the presence of an acid with a trialkyl orthoformate of the formula (IX)

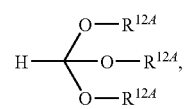
(IX)

in which $R^{12A}$ has the meaning indicated above,
to give a compounds of the formula (X-A)

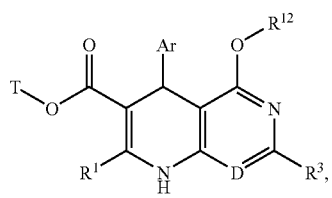
(X-A)

in which Ar, D, T, $R^1$, $R^3$ and $R^{12}$ each have the meanings indicated above,
or reacting the compounds of the formula (VI) in an inert solvent in the presence of a base with a compound of the formula (XI)

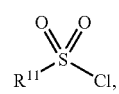
(XI)

in which $R^{11}$ has the meaning indicated in claim 1,
to give a compound of the formula (X-B)

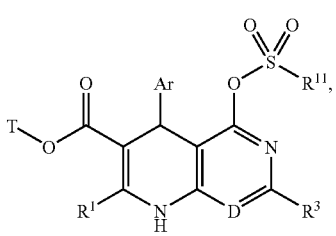
(X-B)

in which Ar, D, T, R¹, R³ and R¹¹ each have the meanings indicated above, eliminating the ester group T in the compounds of the formula (X-A) or (X-B) to give a carboxylic acids of the formula (XII)

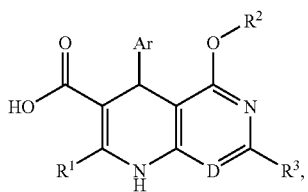
(XII)

in which Ar, D, R¹, R² and R³ each have the meanings indicated in claim 1, then converting the compound of formula (CII) with 1,1'-carbonyldiimidazole into the imidazolides of the formula (XIII)

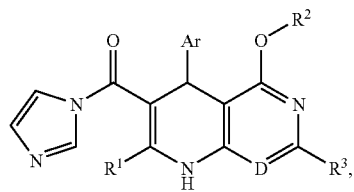
(XIII)

in which Ar, D, R¹, R² and R³ each have the meanings indicated above,
and reacting the compound of formula (XIII) in an inert solvent, optionally in the presence of an auxiliary base, with ammonia to give an amide of the formula (I), optionally, separating compounds of the formula (I) produced as described above by method known to the skilled worker into their enantiomers and/or diastereomers, and, optionally, converting the compound of formula (I) with an appropriate (i) solvent and/or (ii) base or acid into a salt thereof.

7. A pharmaceutical composition comprising a compound of the formula (I) as defined in claim 1 in combination with an inert, non-toxic, pharmaceutically suitable excipient.

8. The pharmaceutical composition of claim 7 further comprising one or more further active ingredients selected from the group consisting of ACE inhibitors, renin inhibitors, angiotensin II receptor antagonists, beta-blockers, acetylsalicylic acid, diuretics, calcium antagonists, statins, digitalis (digoxin) derivatives, calcium sensitizers, nitrates and antithrombotics.

9. The pharmaceutical composition as claimed in claim 7 for the treatment of aldosteronism, high blood pressure, chronic heart failure, the sequelae of a myocardial infarction, cirrhosis of the liver, renal failure and stroke.

10. A compound having the following structure:

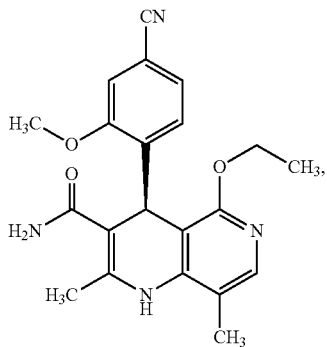 [SMILES: CCOc1ncc(C)c2c1[C@H](c1ccc(C#N)cc1OC)C(C(N)=O)=C(C)N2]

or a salt thereof.

* * * * *

UNITED STATES PATENT AND TRADEMARK OFFICE
CERTIFICATE OF CORRECTION

PATENT NO. : 8,436,180 B2  
APPLICATION NO. : 12/526951  
DATED : May 7, 2013  
INVENTOR(S) : Bärfacker et al.

Page 1 of 2

It is certified that error appears in the above-identified patent and that said Letters Patent is hereby corrected as shown below:

In the Specification  
In Column 12, Lines 60-61, delete "1,4-diazabicycl," and insert -- 1,4-diazabicyclo --, therefor.  
In Column 21, Line 11, delete "aminone" and insert -- amrinone --, therefor.  
In Column 21, Lines 39-40, delete "chlorthiazide, hydrochlorthiazide," and insert -- chlorothiazide, hydrochlorothiazide, --, therefor.  
In Column 22, Line 14, delete "carazalol," and insert -- carazolol, --, therefor.  
In Column 23, Line 42, delete "colesolvam," and insert -- colesevelam, --, therefor.  
In Column 29, Line 42, delete "(Elpos):" and insert -- (EIpos): --, therefor.  
In Column 30, Line 9, delete "(Elpos):" and insert -- (EIpos): --, therefor.  
In Column 30, Line 42, delete "(Elpos):" and insert -- (EIpos): --, therefor.  
In Column 31, Line 13, delete "(Elpos):" and insert -- (EIpos): --, therefor.  
In Column 31, Line 47, delete "(Elpos):" and insert -- (EIpos): --, therefor.  
In Column 34, Line 5, delete "(Elpos):" and insert -- (EIpos): --, therefor.  
In Column 34, Line 38, delete "(Elpos):" and insert -- (EIpos): --, therefor.  
In Column 34, Line 67, delete "(Elpos):" and insert -- (EIpos): --, therefor.  
In Column 35, Line 42, delete "(Elpos):" and insert -- (EIpos): --, therefor.  
In Column 36, Line 20, delete "(Elpos):" and insert -- (EIpos): --, therefor.  
In Column 36, Line 66, delete "(Elpos):" and insert -- (EIpos): --, therefor.  
In Column 37, Line 38, delete "(Elpos):" and insert -- (EIpos): --, therefor.  
In Column 38, Line 10, delete "(Elpos):" and insert -- (EIpos): --, therefor.  
In Column 38, Line 44, delete "(Elpos):" and insert -- (EIpos): --, therefor.  
In Column 39, Line 9, delete "(Elpos):" and insert -- (EIpos): --, therefor.  
In Column 39, Line 41, delete "(Elpos):" and insert -- (EIpos): --, therefor.  
In Column 40, Line 16, delete "(Elpos):" and insert -- (EIpos): --, therefor.  
In Column 40, Line 66, delete "(Elpos):" and insert -- (EIpos): --, therefor.  
In Column 41, Line 38, delete "(Elpos):" and insert -- (EIpos): --, therefor.  
In Column 42, Line 15, delete "(Elpos):" and insert -- (EIpos): --, therefor.  
In Column 42, Line 62, delete "(Elpos):" and insert -- (EIpos): --, therefor.  
In Column 43, Line 37, delete "(Elpos):" and insert -- (EIpos): --, therefor.  
In Column 44, Line 15, delete "(Elpos):" and insert -- (EIpos): --, therefor.

Signed and Sealed this  
First Day of July, 2025

Coke Morgan Stewart  
*Acting Director of the United States Patent and Trademark Office*

CERTIFICATE OF CORRECTION (continued)
U.S. Pat. No. 8,436,180 B2

In Column 44, Line 62, delete "(Elpos):" and insert -- (EIpos): --, therefor.
In Column 45, Line 37, delete "(Elpos):" and insert -- (EIpos): --, therefor.
In Column 46, Line 11, delete "(Elpos):" and insert -- (EIpos): --, therefor.
In Column 46, Line 62, delete "(Elpos):" and insert -- (EIpos): --, therefor.
In Column 47, Line 34, delete "(Elpos):" and insert -- (EIpos): --, therefor.
In Column 48, Line 20, delete "(Elpos):" and insert -- (EIpos): --, therefor.
In Column 49, Line 9, delete "(Elpos):" and insert -- (EIpos): --, therefor.
In Column 49, Line 62, delete "(Elpos):" and insert -- (EIpos): --, therefor.
In Column 50, Line 35, delete "(Elpos):" and insert -- (EIpos): --, therefor.
In Column 51, Line 7, delete "(Elpos):" and insert -- (EIpos): --, therefor.
In Column 51, Line 62, delete "(Elpos):" and insert -- (EIpos): --, therefor.
In Column 53, Line 20, delete "(Elpos):" and insert -- (EIpos): --, therefor.
In Column 53, Lines 58-59, delete "poly(N-methacryloyl-D-leucine dicyclopropylmethylamide;" and insert -- poly(N-methacryloyl-D-leucine-dicyclopropylmethylamide); --, therefor.
In Column 53, Lines 64-65, delete "poly(N-methacryloyl-D-leucine-dicyclopropylmethylamide;" and insert -- poly(N-methacryloyl-D-leucine-dicyclopropylmethylamide); --, therefor.
In Column 54, Lines 7-8, delete "poly(N-methacryloyl-D-leucine-dicyclopropylmethylamide;" and insert -- poly(N-methacryloyl-D-leucine-dicyclopropylmethylamide); --, therefor.
In Column 54, Line 61, delete "(Elpos):" and insert -- (EIpos): --, therefor.
In Column 55, Line 38, delete "(Elpos):" and insert -- (EIpos): --, therefor.
In Column 56, Line 14, delete "(Elpos):" and insert -- (EIpos): --, therefor.
In Column 56, Line 64, delete "(Elpos):" and insert -- (EIpos): --, therefor.

In the Claims

In Column 68, Line 12, in Claim 6, delete "$R^{12}A$" and insert -- $R^{12A}$ --, therefor.
In Column 68, Line 29, in Claim 6, delete "compounds" and insert -- compound --, therefor.
In Column 68, Line 43, in Claim 6, delete "compounds" and insert -- compound --, therefor.
In Column 69, Line 4, in Claim 6, delete "acids" and insert -- acid --, therefor.